United States Patent
Lipinski et al.

(10) Patent No.: US 8,936,843 B2
(45) Date of Patent: Jan. 20, 2015

(54) THIN, SMOOTH NITRILE RUBBER GLOVES

(75) Inventors: Timothy M. Lipinski, Songkhla (TH); Choong Kheng Tang, Kedah (MY)

(73) Assignee: Avent, Inc., Alpharetta, GA (US)

( * ) Notice: Subject to any disclaimer, the term of this patent is extended or adjusted under 35 U.S.C. 154(b) by 311 days.

(21) Appl. No.: 13/060,198

(22) PCT Filed: Aug. 27, 2009

(86) PCT No.: PCT/IB2009/053758
§ 371 (c)(1), (2), (4) Date: Apr. 29, 2011

(87) PCT Pub. No.: WO2010/023634
PCT Pub. Date: Mar. 4, 2010

(65) Prior Publication Data
US 2011/0191936 A1     Aug. 11, 2011

Related U.S. Application Data

(60) Provisional application No. 61/092,300, filed on Aug. 27, 2008.

(51) Int. Cl.
| | |
|---|---|
| C08L 13/02 | (2006.01) |
| A41D 19/00 | (2006.01) |
| A61B 19/04 | (2006.01) |
| C08J 5/02 | (2006.01) |
| C08L 9/04 | (2006.01) |

(52) U.S. Cl.
CPC .............. *C08L 13/02* (2013.01); *A41D 19/0062* (2013.01); *A61B 19/04* (2013.01); *C08J 5/02* (2013.01); *C08L 9/04* (2013.01); *C08J 2309/04* (2013.01)
USPC .............................. 428/35.7; 2/161.7; 2/161.8

(58) Field of Classification Search
CPC ........... A41D 10/0062; A41D 19/0003; A41D 19/0006; A41D 19/0055; A41D 19/0096; A41D 19/00; A61B 19/04; C08J 5/00; C08J 5/005; C08J 5/02
USPC .................. 428/35.7; 2/161.7, 161.8; 264/130
See application file for complete search history.

(56) References Cited

U.S. PATENT DOCUMENTS

| | | | |
|---|---|---|---|
| 5,014,362 A | 5/1991 | Tillotson et al. | |
| 5,357,636 A | 10/1994 | Dresdner, Jr. et al. | |
| 5,486,322 A * | 1/1996 | Fuchs | 264/46.5 |

(Continued)

FOREIGN PATENT DOCUMENTS

EP      1 260 549 A1    11/2002

*Primary Examiner* — Gwendolyn Blackwell
*Assistant Examiner* — Yan Lan
(74) *Attorney, Agent, or Firm* — Dority & Manning, P.A.

(57) ABSTRACT

A nitrile-rubber medical exam glove composed of a glove body which is a flexible layer of nitrile-butadiene rubber having a chlorinated first surface forming a donning side and an un-chlorinated second surface forming a grip side. The elastomeric glove also includes a substantially uniform distribution of a release agent distributed over the un-chlorinated second surface of the glove body. The elastomeric glove has: (a) an average thickness of between about 0.03 to 0.12 mm in a palm region of the glove body as measured in accordance with ASTM D3767, procedure A; (b) an un-chlorinated second surface of the glove body characterized by a Surface Root Mean Square Roughness of from about 3.00 μm to about 6.55 μm; and (c) a failure rate of less than about 1 percent when the elastomeric glove is subjected to pinhole leak testing generally in accordance with ASTM D5151-06.

14 Claims, 11 Drawing Sheets

(56) References Cited

U.S. PATENT DOCUMENTS

| | | | |
|---|---|---|---|
| 6,566,435 B1 * | 5/2003 | Teoh et al. | 524/432 |
| 7,176,260 B2 | 2/2007 | Tao | |
| 2006/0070167 A1 | 4/2006 | Eng et al. | |
| 2006/0257674 A1 * | 11/2006 | Lipinski et al. | 428/451 |
| 2007/0033704 A1 | 2/2007 | Wang | |
| 2008/0139723 A1 | 6/2008 | Foo | |

* cited by examiner

THIN, SMOOTH NITRILE RUBBER GLOVES

CROSS-REFERENCE TO RELATED APPLICATIONS

This application is the national stage of International Application No. PCT/IB2009/053758, filed Aug. 27, 2009, which claims priority to U.S. Provisional Application No. 61/092,300, filed Aug. 27, 2008, the disclosures of which are hereby incorporated by reference.

FIELD OF INVENTION

The present invention pertains to flexible synthetic rubber medical exam gloves and methods of making such gloves.

BACKGROUND

The development of modern synthetic rubber materials have made possible the manufacture of a wide variety of elastomeric articles having varying properties of strength and chemical resistance. Among these articles are gloves designed for either industrial or medical uses. As safety accessories, industrial and medical gloves protect a user from environmental hazards such as chemicals or pathogens. In particular, medical gloves contribute to sanitary hospital conditions by limiting exposure of patients to potentially infectious matter, and serve to protect health professionals from disease transmission through contact with body fluids.

Relatively thin and flexible industrial or medical gloves have traditionally been made of natural rubber latex in a dipping process. The donning surface (i.e., the interior) of these gloves is conventionally coated with corn starch, talcum, or lypcopodium powder to lubricate the gloves, making them easier to don. In recent years, powder-free work gloves and medical gloves have largely replaced powdered gloves because of changing needs and perceptions of glove consumers. For example, cornstarch or other powders can impede healing if it gets into tissue (as during surgery). Similarly, powders are unsuitable for clean rooms such as those used in the manufacture of semiconductors and electronics.

Glove consumers have been moving away from natural rubber gloves due, in part, to an increasing rate of significant allergic reactions to proteins in natural rubber latex among health professionals as well as the general population. The industry has increasingly moved to latex emulsions based on synthetic rubber materials. While hospitals, laboratories, or other work environments that use rubber gloves often want to go "latex free" to better protect their workers, the higher cost of non-latex products, such as nitrile rubber, often limits their ability to make the change. For example, nitrile rubber gloves may cost two or more times the price of the natural rubber latex or vinyl-based counterparts. This fact has often caused purchasers in cost-sensitive environments, such as many hospitals, either to switch to less expensive polyvinyl chloride gloves or prevented them from switching to the synthetic materials.

In addition to being more expensive, nitrile-butadiene rubber medical exam gloves are typically stiffer and are perceived as much less comfortable to wear in comparison to similar gloves made from natural rubber latex materials. For instance, natural rubber latex (NRL) medical exam gloves typically require a stress of about 2.5 MPa (362.5 psi) to stretch to an elongation of about 300 percent of its original dimensions. This often is referred to as the glove's 300 percent modulus. Nitrile rubber medical exam gloves, on the other hand, typically require more than twice that amount of stress (~6-8 MPa, ~870-1160 psi) to achieve the same 300 percent elongation. While polyvinyl chloride medical exam gloves can be inexpensive, polyvinyl chloride medical exam gloves are typically considered a lower performance choice. That is, polyvinyl chloride medical exam gloves are typically stiffer and less elastic than even the conventional thicker nitrile rubber medical exam gloves.

Several previous approaches to softening nitrile rubber medical exam gloves involved strongly limiting or completely omitting zinc oxide and other materials capable of ionically crosslinking carboxylated nitrile rubber, such as those described in U.S. Pat. Nos. 6,031,042 and 6,451,893. In addition to not yielding force-strain properties similar to those of comparable natural rubber medical exam gloves, this method requires higher curing temperatures, a need for higher levels of other chemicals that may cause skin irritation, or may lead to processing difficulties such as thickening of the nitrile latex before dipping.

Other approaches to making a nitrile-butadiene rubber medical exam glove more comfortable, such as those described in U.S. Pat. Nos. 5,014,362 and 6,566,435, have relied on stress relaxation over time and require constantly applied levels of strain to cause that relaxation or softening. Such determination measures are difficult to maintain and are considered impractical or economically unfeasible.

While it might seem that a practical solution to the expense of conventional nitrile rubber medical exam gloves would be to make nitrile rubber medical exam gloves thinner than conventional nitrile rubber medical exam gloves (e.g., about 0.11 to about 0.20 mm in thickness at the palm region of the glove as measured generally in accordance with ASTM D3767, procedure A), there are significant problems associated with making nitrile rubber medical exam gloves that are thinner than conventional nitrile rubber medical exam gloves. A primary problem is pinhole formation which is sometimes referred to as "pinholes" or "pinhole defects. The lack of a thin nitrile rubber medical exam glove in the marketplace actually highlights the difficulties of economically and effectively solving these problems.

In the field of dipped rubber articles and in the field of breathable, stretched micro-porous films, a conventional solution to pinhole defects is to utilize multiple thin layers of material. For example, PCT International Publication WO 1999/030904 A1 proposes in the manufacture of thin breathable films such as stretched micro-porous films that the use of a multilayer film greatly reduces or eliminates the probability of an imperfection (i.e., a pinhole) in any one area of one layer of the film aligning with an imperfection (i.e., a pinhole) in the other layer of the film, thereby substantially increasing the probability that the material produced will meet ASTM barrier test requirements. However, forming multilayer thin films adds complexity and expense to the manufacturing process and defeats the cost advantages provided by making an article thinner.

Similarly, U.S. Patent Application Publication No. 2008/0138723 A1 discloses nitrile rubber latex formulations and a process to make a multi-layered elastic glove in which the thickness of the multi-layered glove is between 0.01 mm and 0.3 mm. Such a multiple thin-layer dipping process to form thin multilayered gloves adds significant complexity and expense to the manufacturing process and defeats the cost advantages provided by making an article thinner. Importantly, the lack of a thin multi-layer nitrile rubber medical exam glove in the marketplace actually highlights the difficulties of economically and effectively solving these problems.

Although comparatively inexpensive, polyvinyl chloride medical exam gloves have a number of shortcomings. The shortcomings of polyvinyl chloride medical exam gloves include: being relatively inelastic; having relatively low tensile strength; having relatively greater amounts of pinhole defects; and leaching certain toxic components. These shortcomings can result in less comfort for the wearer, a weaker glove with higher permeability or poorer barrier protection against some common chemicals, and harm to the user and/or environment. Polyvinyl chloride medical exam gloves typically have a leakage percentage rate of from about 16 percent to about 44 percent when subjected to conventionally accepted leak testing. Conventional nitrile rubber medical exam gloves exhibit leakage percentage rates of less than 7 percent, typically less than about 5 percent or even lower (e.g., less than 2 percent). Reports of this comparative testing may be found at, for example, Kerr L. N., Chaput M. P., Cash L. C., et al., 2004 September. Assessment of the Durability of Medical Examination Gloves, *Journal of Occupational and Environmental Hygiene* 1: 607-612; Kerr L. N., Boivin W. S., Chaput M. P., et al., 2002 September. The Effect of Simulated Clinical Use on Vinyl and Latex Exam Glove Durability. *The Journal of Testing and Evaluation* 30(5):415-420; Korniewicz D. M., El-Masri M., Broyles J. M., et al., 2002 April. Performance of Latex and Nonlatex Medical Examination Gloves during Simulated Use. *American Journal of Infection Control,* 30(2):133-8; and Rego A., Roley L., 1999 October. In-Use Barrier Integrity of Gloves: Latex and Nitrile Superior to Vinyl. *American Journal of Infection Control,* 27(5):405-410. Given that polyvinyl chloride is inherently a much weaker material in terms of tensile strength and is likely to have pinholes in the membrane, polyvinyl chloride medical exam gloves require the use of a greater amount of material to achieve the same level of strength and integrity as a nitrile rubber medical exam glove. In view of these and other factors, consumers are beginning to seek an alternative to polyvinyl chloride gloves.

A need exists for an inexpensive, nitrile rubber glove that has good barrier properties at a cost that is less expensive than traditional nitrile rubber gloves or comparable to polyvinyl chloride gloves. Moreover, a need exists for an inexpensive nitrile rubber medical exam glove that can successfully provide the benefits of nitrile rubber materials while also providing pliability or softness like natural rubber latex without the conditions required for softening caused by stress relaxation. The present invention provides a simple solution to this need by means of a modified nitrile rubber-based synthetic polymer that exhibits not only good chemical resistance, but also stretch and silky tactile characteristics similar to natural rubber latex.

SUMMARY OF THE INVENTION

The present invention offers an economical solution to the needs outlined above by providing a nitrile rubber glove, such as a nitrile-rubber medical exam glove, that exhibits not only good chemical resistance, but also force to stretch characteristics and silky tactile characteristics similar to natural rubber latex gloves, pinhole defect performance similar to nitrile-rubber medical exam gloves of conventional thicknesses, and relatively low cost similar to polyvinyl chloride gloves.

The present invention relates to an elastomeric glove composed of a glove body which is a flexible layer of an elastomeric nitrile rubber (i.e., nitrile-butadiene rubber) formed from nitrile rubber latex (i.e., nitrile-butadiene rubber latex). Desirably, the glove body is a single layer of an elastomeric nitrile-butadiene rubber. That is, the glove body may consist of a single layer of an elastomeric nitrile-butadiene rubber. In other words, the elastomeric glove may be composed of a glove body that is a single layer of elastomeric nitrile-butadiene rubber and the glove body may itself have applied layers or coatings of other materials such as release agents, donning layers, donning agents, silicone materials and the like. The glove body has a chlorinated first surface forming a donning side of the glove body and an un-chlorinated second surface forming a grip side of the glove body. The elastomeric glove also includes a substantially uniform distribution of a release agent, typically a metallic salt of a fatty acid, distributed over the un-chlorinated second surface of the glove body.

According to the invention, the elastomeric glove has: (a) an average thickness of between about 0.03 to 0.12 mm in a palm region of the glove body as measured in accordance with ASTM D3767, procedure A; (b) an un-chlorinated second surface of the glove body characterized by a Surface Root Mean Square Roughness of from about 3.00 µm to about 6.55 µm; and (c) a failure rate of less than about 1 percent when the elastomeric glove is subjected to pinhole leak testing generally in accordance with ASTM D5151-06. That is, when a sample of gloves (e.g., 100 or 1000 or even more) are tested in accordance with ASTM D5151-6 which is a "pass-fail" test procedure, less than about 1 percent of the gloves in the sample will fail. For example, the elastomeric glove desirably has a failure rate of less than about 0.5 percent when the elastomeric glove is subjected to pinhole leak testing generally in accordance with ASTM D5151-06. As another example, the elastomeric glove desirably has a failure rate of less than about 0.1 percent when the elastomeric glove is subjected to pinhole leak testing generally in accordance with ASTM D5151-06.

Desirably, the un-chlorinated second surface of the glove body is characterized by a Surface Root Mean Square Roughness of about 3.00 µm to about 5.30 µm. In an aspect of the invention, the un-chlorinated second surface of the glove body is characterized by a Surface Root Mean Square Roughness of less than about 3.0 µm. According to the invention, the glove may have an average thickness as determined in accordance with ASTM D3767, procedure A, ranging from about 0.025 or 0.03 mm to about 0.15 mm, typically from about 0.04 mm to about 0.13 mm, or from about 0.045 or 0.05 mm to about 0.08 or 0.10 mm. According to certain embodiments, the substrate has a thickness in the palm region of from about 0.045 mm to about 0.7 mm, or from about 0.05 mm to about 0.9 mm; or from about 0.05 mm to about 0.07 mm.

One feature of the present invention is that the glove body exhibits a force-to-strain response from zero elongation to 300 percent elongation (F-300) of less than or equal to about 1.50 N at F-300 when tested in accordance with ASTM D412-06. For example, the glove body desirably exhibits a force-to-strain response when elongated from zero elongation to 300 percent elongation (F-300) that ranges from about 1.08 N to about 1.45 N for a thickness of about 0.03-0.10 mm when tested in accordance with ASTM D412-06. The glove body desirably exhibits a force-to-strain response during elongation from zero elongation to 400 percent elongation (F-400) of less than about 2 N at F-400 when tested in accordance with ASTM D412-06, or the glove body exhibits a force-to-strain response during elongation from zero elongation to 500 percent elongation (F-500) of less than about 2 N at F-500 when tested in accordance with ASTM D412-06. In an aspect of the present invention, the glove body exhibits a force to break of less than about 6.0 N at about 560 percent elongation to about 600 percent elongation of an original dimension when tested in accordance with ASTM D412-06. These tensile strength characteristics are important for providing a practical and useful glove, particularly when combined with the relatively low glove thickness and the good performance in pinhole leak testing generally in accordance with ASTM D5151-06.

In another aspect of the invention, the glove body has a surface area to volume ratio of greater than 84/cm. For example, the glove body may have a surface area to volume ratio of about 200/cm or greater. As another example, the glove body may have a surface area to volume ratio between about 150/cm to about 250/cm. As another example, the glove body may have a surface area to volume ratio of less than about 400/cm.

In yet another aspect of the invention, the un-chlorinated outer or "grip" surface of the glove body has a pore density of greater than or equal to about 800 pores per $mm^2$ as determined by optical image analysis. That is, the number of a concave dimples or pits (generally referred to as "pores") located on the un-chlorinated outer (grip) surface of the glove body is greater than or equal to about 800 pores per $mm^2$ as determined by optical image analysis techniques. For example, the un-chlorinated outer or "grip" surface of the glove body may have a pore density ranging from about 820 per $mm^2$ to about 1600 per $mm^2$ as determined by optical image analysis. It is contemplated that the un-chlorinated outer or "grip" surface of the glove body may have a pore density greater than about 1600 per $mm^2$. In other examples, the un-chlorinated outer or "grip" surface of the glove body may have a pore density that ranges from about 850 per $mm^2$ to about 1450 per $mm^2$. In yet other examples, the un-chlorinated outer or "grip" surface of the glove body may have a pore density that ranges from about 900 per $mm^2$ to about 1280 per $mm^2$.

The release agent distributed over the un-chlorinated second surface of the glove body is selected from metallic salts of a fatty acid, petroleum waxes with a melting point of less than about 200° C., natural animal waxes, or synthetic waxes. Desirably, the release agent is a metallic salt of a fatty acid such as metallic stearates. Even more desirably, the release agent is a metallic stearate such as calcium stearate.

In an aspect of the invention, the elastomeric nitrile-butadiene rubber is a terpolymer of acrylonitrile, butadiene, and carboxylic acid in which the acrylonitrile polymer content is about 15 percent, by weight, to about 42 percent, by weight, the carboxylic acid content is between about 1 percent, by weight and about 10 percent by weight, and the remaining portion of the terpolymer composition is butadiene. For example, the terpolymer may contain about 20 percent to about 40 percent acrylonitrile polymer, about 3 percent to about 8 percent carboxylic acid, and about 40 percent to about 65 or 67 percent is butadiene. Desirably, the terpolymer may contain about 20 percent to about 30 percent acrylonitrile polymer, about 4 percent to about 6 percent carboxylic acid, and the remaining balance is predominately butadiene (e.g., from about 64 percent to about 76 percent).

The present invention also encompasses a process for making an elastomeric glove. The process includes the following steps:

coating a surface of a mold with a coagulant solution and a release agent, the coagulant solution having a calcium ion concentration of between about 3 percent and about 5 percent based on the weight of calcium ions in the coagulant solution;

partially drying the mold coated with the coagulant solution and waxy release agent;

immersing the partially dried mold into an nitrile-butadiene rubber latex emulsion having a latex solids content of between about 12 percent and about 20 percent, by weight, for a dwell time of between about 7 seconds and 15 seconds to form a layer of coagulated nitrile-butadiene rubber latex on the mold surface;

removing the mold from the nitrile-butadiene rubber latex emulsion;

immersing the mold containing the coagulated nitrile-butadiene rubber latex into an aqueous bath to remove excess calcium ions and then drying the coagulated nitrile-butadiene rubber latex to form a glove body on the mold;

immersing the mold containing the glove body into a chlorinating bath to chlorinate an exterior surface of the glove body on the mold; and removing the glove body from the mold by inverting the glove body such that the chlorinated exterior surface of the glove body forms an interior surface of the glove and an un-chlorinated interior surface of the glove body forms an exterior surface of the glove.

According to the invention, the nitrile-butadiene rubber latex emulsion may have latex solids content of between about 14 percent and about 20 percent, by weight. Desirably, the nitrile-butadiene rubber latex emulsion may have a latex solids content of between about 15 percent and about 19 percent. Even more desirably, the nitrile-butadiene rubber latex emulsion may have a latex solids content of between about 16 percent and about 18 percent. The dwell time that the partially dried mold is immersed into an nitrile-butadiene rubber latex emulsion may be between about 7 seconds and 13 seconds to form a layer of coagulated polymer on the mold surface. Desirably, the dwell time that the partially dried mold is immersed into an nitrile-butadiene rubber latex emulsion may be between about 8 seconds and 12 seconds to form a layer of coagulated nitrile-butadiene rubber latex on the mold surface. According to an aspect of the invention, the mold coated with the coagulant solution and waxy release agent is immersed into an nitrile-butadiene rubber latex emulsion only a single time to form a single layer of nitrile-butadiene rubber latex.

In an aspect of the invention, the nitrile-butadiene rubber latex emulsion is desirably one in which the elastomeric nitrile-butadiene rubber is a terpolymer of acrylonitrile, butadiene, and carboxylic acid in which the acrylonitrile polymer content is about 20 percent, by weight, to about 30 percent, by weight, the carboxylic acid content is between about 4 percent, by weight and about 6 percent by weight, and the remaining portion of the terpolymer composition is butadiene.

Additional features and advantages of the present invention will be revealed in the following detailed description. Both the foregoing summary and the following description are merely representative of the invention and are an overview for understanding the invention as claimed.

BRIEF DESCRIPTION OF FIGURES

FIG. 2A illustrates the characteristics of an exemplary surface of an elastomeric medical exam glove according to the present invention. FIG. 2B illustrates the surface features of a comparative, commercially available, nitrile rubber medical exam glove.

FIG. 8A illustrates the frequency of pores having a specified equivalent circular diameter as determined by optical image analysis for an exemplary surface of a nitrile-butadiene rubber medical exam glove according to the present invention. FIG. 8B illustrates the frequency of pores having a specified equivalent circular diameter as determined by optical image analysis for an exemplary surface of a comparative, commercially-available nitrile-butadiene rubber medical exam glove.

DETAILED DESCRIPTION OF THE INVENTION

Figure 1A:
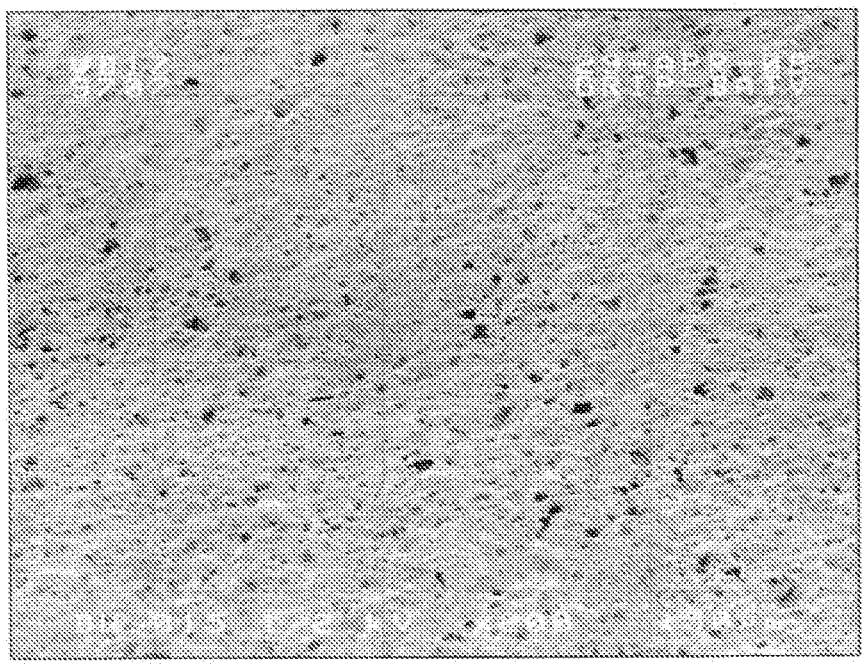
FIGS. 1A and 1B are scanning electron microscopy (SEM) photomicrographs, both at a linear magnification level of 200×, of the un-chlorinated outermost side of two different nitrile rubber medical exam gloves. The surface features of an exemplary elastomeric medical exam glove according to the present invention is illustrated in FIG. 1A and the surface features of a comparative, commercially available, nitrile rubber medical exam glove is illustrated in FIG. 1B.

A desirable attribute for elastomeric articles that are worn on the body is softness or pliability of the polymeric material. The present invention describes the creation of elastic articles, such as gloves, made from a nitrile polymer formulation. As used herein, the terms "elastic" or "elastomeric" generally refer to a material that, upon application of a force, is stretchable to an extended, biased length. Upon release of the stretching, biasing force, the material will substantially recover to near net shape or original dimensions.

Nitrile-butadiene rubber (commonly referred to as "nitrile rubber" or "NBR") is a family of amorphous unsaturated copolymers of acrylonitrile and various butadiene monomers (1,2-butadiene and 1,3-butadiene). This form of synthetic rubber is generally resistant to aliphatic hydrocarbons, such as fatty tissue, oils, and other chemicals. Nitrile-butadiene rubber has been used to create molded goods, footwear, adhesives, sealants, sponge, expanded foams, and floor mats. Its resilience makes conventional nitrile-butadiene rubber a good material for disposable gloves used in laboratory, cleaning, industrial work, and clinical situations. Conventional medical exam gloves made from conventional nitrile-butadiene rubber generally are three times more puncture-resistant than conventional medical exam gloves made from natural rubber (i.e., formed from natural rubber latex) or polyvinyl chloride.

Although gloves made from conventional nitrile-butadiene rubber are more resistant to oils and acids than gloves made from natural rubber latex, traditionally gloves made from conventional nitrile-butadiene rubber have inferior strength and flexibility in comparison to gloves that are essentially identical except for being made from natural rubber latex. The present invention utilizes a modified nitrile-butadiene rubber formulation and a modified glove manufacturing process to address drawbacks of gloves made from conventional nitrile-butadiene rubber. The modified nitrile-butadiene rubber formulation and modified glove manufacturing process is used to produce thin, flexible elastomeric gloves that demonstrate unique physical characteristics. Of course, the modified nitrile-butadiene rubber formulation and a modified glove manufacturing process may be adapted for the fabrication of other dipped-goods such as, for example, balloons, membranes and the like.

As a disposable product, a nitrile-butadiene rubber glove made according to the present invention will have a mass that is at least about 40-50% less than a typical polyvinyl chloride-based glove of the same type (e.g., medical exam, household, or industrial) and size (i.e., small, medium, large, x-large). For example, a nitrile-butadiene rubber medical exam glove according to the present invention that is made to the conventional size "M" or "Medium" will have a mass that is at least about 40 percent to about 50 percent less (or an even greater percentage less) than a typical polyvinyl chloride medical exam glove that is made to the conventional size "M" or "Medium".

As previously noted, various published reports describing comparative testing of conventional polyvinyl chloride medical exam gloves and nitrile-butadiene rubber medical exam gloves show that polyvinyl chloride medical exam gloves have a greater incidence of leakage. Given that vinyl is inherently a much weaker material in terms of tensile strength and is likely to have pinholes in the membrane, vinyl-based medical exam gloves require the use of a greater amount of material to achieve the same level of strength and integrity as a nitrile-butadiene rubber medical exam glove of the present invention. Thus, the nitrile-butadiene rubber medical exam gloves of the present invention contribute relatively less waste and have less environmental impact because they have substantially less mass than comparable polyvinyl chloride medical exam gloves.

From a commercial viewpoint, the nitrile-butadiene rubber medical exam gloves of the present invention are cost competitive with inexpensive polyvinyl chloride medical exam gloves. That is, the thinner nitrile-butadiene rubber gloves of the present invention are more affordable than conventional nitrile-butadiene rubber gloves that are thicker products. The relatively lower cost of the thinner nitrile-butadiene rubber gloves of the present invention provides more opportunities for consumers to switch from polyvinyl chloride gloves to a better performing nitrile-butadiene rubber glove (e.g., fewer pinhole defects and better stretch/tensile properties) without much adverse economic impact in addition to avoiding exposure to hazardous components such as diethylhexylopthalate (DEHP) which can leach from polyvinyl chloride gloves.

As noted above, manufacturers in the glove industry have not previously developed thinner, economical nitrile-butadiene rubber gloves because it was generally believed that barrier properties of the nitrile-butadiene rubber glove would be compromised by the thinness of the material and given the relative low cost of vinyl-based gloves, nitrile-butadiene rubber gloves would be non-competitive in that segment of the market. Contrary to such beliefs, the present invention is directed to a thinner economical nitrile-butadiene rubber glove (i.e., an average thickness between about 0.025 or 0.03 mm to about 0.15 mm, typically from about 0.05 mm to about 0.13 mm, or from about 0.05 or 0.06 mm to about 0.08 or 0.10 mm as determined in accordance with ASTM D3767, procedure A) with satisfactory barrier performance and force to stretch properties.

For example, the elastomeric glove desirably has a failure rate of less than about 1 percent when the elastomeric glove is subjected to pinhole leak testing generally in accordance with ASTM D5151-06. This means that when a sample of gloves (e.g., 100 gloves, 500 gloves, 1000 gloves, or 10,000 gloves or even more) are tested in accordance with ASTM D5151-6 which is a "pass-fail" test procedure, less than about 1 percent of the gloves in the sample will fail. As another example, the elastomeric glove desirably has a failure rate of less than about 0.5 percent or even less than about 0.1 percent when the elastomeric glove is subjected to pinhole leak testing generally in accordance with ASTM D5151-06.

Although physical and chemical properties vary depending on the nitrile-butadiene rubber composition (the more acrylonitrile within the polymer, the higher the resistance to oils but the lower the flexibility of the material), the present invention combines soft, flexible elastomeric characteristics with satisfactory levels of strength. In an aspect of the invention, these desirable properties are also combined with satisfactory levels of breathability as described or characterized by conventional Water Vapor Transmission Rate (WVTR) testing.

The nitrile-butadiene rubber composition according to the present invention is desirably a random terpolymer of acrylonitrile, butadiene, and a carboxylic acid, such as a methacrylic acid. The composition includes, in terms of weight percent (wt. %) of the major components: about 15% to about 42% acrylonitrile polymer; about 1% to about 10% carboxylic acid, and the remaining balance is predominately butadiene (e.g., about 38% to about 75%). Typically, the composition is: about 20-40% acrylonitrile polymer, about 3-8% carboxylic acid, and about 40%-65% or 67% is butadiene. Particular compositions include a terpolymer of acrylonitrile butadiene and carboxylic acid in which the acrylonitrile content is less than about 35% and carboxylic acid is less than about 10%, with butadiene content being the remaining balance. More desirable composition can have a range of: about 20-30% acrylonitrile polymer, about 4-6% carboxylic acid, and the remaining balance is predominately butadiene. Processing or other component ingredients may be either optional or present up to about 20% (i.e., 20 weight percent) of the total composition; typically in amounts ranging from about 0.1 to about 17%. These other ingredients may include metallic oxides (e.g., ZnO, MgO) in levels of about 0.25-10%, sulfur or other crosslinking agents (e.g., peroxide, aziridine, acrylates) at levels of 0.001-3%, and accelerators at a level of 0.25 to 2.0%. Any of the various vulcanization accelerators may be use, including, but not limited to thiurams, dithiocarbamates, xanthates, guanidines, or disulfides.

The present invention can be adapted to make a variety of thin-walled dipped goods, such as medical examination or industrial gloves, balloons, condoms, probe covers, dental dams, finger cots, catheters, and the like. Alternatively, the nitrile-butadiene rubber can be incorporated as part of articles such as garments (e.g., shirts, pants, gowns, coveralls, headwear, shoe covers) or draping materials. The general process for making dipped elastic rubber products is well known to those in the art, and will not be reviewed in detail herein. For example, U.S. Pat. Nos. 6,673,871, 7,041,367, or 7,178,171, the contents of which are incorporated herein by reference, each describe exemplary processes for making a dipped elastic rubber glove. However, the present invention also relates to a process for fabricating thin elastomeric membranes, films and articles that is an improvement over the conventional processes.

Using separate mechanisms, nitrile-butadiene rubber can be crosslinked to generate desired levels of strength and chemical resistance. The first mechanism of crosslinking occurs by ionically bonding carboxylic acid groups together using multivalent metal ions. These ions are typically supplied through addition of zinc oxide to the nitrile-butadiene rubber latex emulsion. Typically, the physical strength and stiffness/softness properties of the polymer are sensitive to this kind of crosslinking. The other crosslinking mechanism is by means of covalent bonding of the butadiene segments of the polymer using, for example, sulfur and rubber accelerator catalysts, which develops good chemical resistance properties.

In the present invention, the extent or amount and types of ionic crosslinking can be controlled by regulating the content of all ionic materials during compounding or formulating of the nitrile-butadiene rubber latex. The crosslinking of the carboxylic acid groups is controlled by the amount and type of ionic materials added to the nitrile-butadiene rubber latex before it us used to produce dipped articles. The thickness of the article can be controlled by a variety of means during the dipping process, such as coagulant concentration, manipulation of the length of time that the mold form dwells in or is covered by the emulsion, temperature, or mechanical rotation or pivoting of the mold after withdraw from the dipping bath.

As with other dipped products, like balloons and condoms, elastomeric nitrile-butadiene rubber gloves are often formed by first coating a mold surface with a coagulant solution, for instance calcium nitrate, then dipping the mold into a polymer latex emulsion to cause gelation of the nitrile rubber over the mold surface. When parameters of a high percentage of latex solids and/or a high concentration of the coagulant are used, the rubber particles gel very quickly to form a coagulated nitrile-butadiene rubber latex layer over the entire latex-coated surface of the mold. A latex emulsion having a solids content of about 35 percent to about 40 percent, by weight, or greater can be referred to as being a relatively "high" solids content latex emulsion. Sometimes the gelation can occur so quickly that the serum (water and aqueous-soluble materials) of the latex are forced out of the glove and appear as transparent drops. This is known as syneresis.

When conventional nitrile-butadiene rubber medical exam gloves are formed, a latex emulsion having conventional levels of latex solids (latex solids content of greater than about 21 percent, by weight up to about 31 or 32 percent, by weight) and a conventional coagulant (i.e., having a coagulating ion concentration of about 6 to 10 percent based on the weight of the coagulation ion in solution) are needed to rapidly form a relatively thick film of nitrile-butadiene latex on the glove mold. The coagulant is generally thought to react most quickly and effectively with the portion of the nitrile-butadiene latex film immediately adjacent the layer of coagulant on the glove mold, and react less thoroughly or effectively with the portion of the nitrile-butadiene latex film away from the layer of coagulant on the glove mold as the coagulant ions are forced to migrate to penetrate further outward into the thickness of the nitrile-butadiene latex film. This phenomenon is believed to result in a glove surface that is less smooth and may also be encountered when multiple thin layers are formed utilizing a multiple latex dip process.

As the parameters of percent latex solids and coagulant concentration are lowered, the gelation will tend to occur more slowly. If the dwell time in the latex emulsion is constant, lowering the percent latex solids and the coagulant concentration typically results in formation of a thinner film layer. When a glove such as a medical exam glove (or other elastomeric membrane) is made according to the present invention, the glove is much smoother or can be characterized as "less rough" on at least the un-chlorinated surface forming a grip side or exterior surface of the finished glove. This smoothness is readily perceptible to ordinary individuals in an unaided comparison of gloves made according to the present invention and conventional nitrile-butadiene rubber gloves.

While the inventors should not be held to any particular theory, it is believed that such a smooth surface produced on a glove of the present invention is the result of using both a weak coagulant and a latex emulsion having a relatively low solids content in a single latex emulsion dip process which appears to cause the nitrile-butadiene latex film to gel more slowly on the mold. Given the nitrile-butadiene latex film layer is thinner than usual, NBR latex particles are believed to react with the coagulant more efficiently and for a longer duration, which allows more time for the latex particles to become more tightly packed together in the film layer. This more compact organization of the latex particles is thought to result in a much smoother glove surface when a single layer of nitrile-butadiene rubber latex is formed on the mold in a single latex dip process.

The polymer latex solids in the nitrile-butadiene latex typically have an average particle size of about 0.08 µm to about 0.20 µm. According to the invention, the nitrile-butadiene polymer latex has a relatively low solids content of between about 14 percent up to about 20 percent, by weight, of nitrile-butadiene polymer solids. Desirably, the nitrile-butadiene polymer latex has a solids content of between about 15 to about 18 percent, by weight.

During the dip process, the glove former is dipped in the nitrile-butadiene rubber latex for a dwell time duration of about 13 seconds or less. Desirably, the dwell time of the single dip is between about 12 seconds and 7 seconds. Even more desirably, the dwell time is between about 7 to 10 seconds.

According to an aspect of the present invention, the particular solids content of the nitrile-butadiene rubber latex influences the associated percentage amount of coagulant applied in the manufacture process. In other words, the amount of coagulating ion present on the glove mold generally corresponds proportionately to the latex solids content in a ratio of about 1:4, however slightly more or less of either may be used depending on the duration of the dwell time of the mold in the latex emulsion. For example, a coagulant solution containing from about 9 to about 12 percent, by weight, calcium nitrate would typically provide approximately from about 3.6 to about 4.8 percent, by weight, calcium ions in the solution. The coagulant ion is thought to transfer to the glove mold at the same concentration it is in solution. Utilizing the coagulating ion concentration to latex solids concentration ration of about 1:4 for this example coagulant solution, the nitrile-butadiene rubber latex should have a solids content of from about 14 to 19 percent, by weight.

According to the present invention, the coagulated substrate or film has a coating of a release agent over at least a portion of an outer surface (or grip side in a glove) of the substrate. The release agent is in the form of a "waxy" material and is used in the fabrication of a powder-free dipped article. The release agent is typically a low-melting organic mixture or compound of high molecular weight, solid at room temperature and generally similar to fats and oils except that it contains no glycerides. For example, the release agent can be: a metallic stearate (e.g., calcium stearate, zinc stearate); a petroleum wax with a melting point of less than about 200° C. (e.g., melting point between about 135° C. to about 180° C.) which can be in the form of paraffin waxes, microcrystalline waxes, or petroleum jelly; a natural animal/insect wax such as bee's wax; or a synthetic wax (e.g., polyethylene waxes). Desirably, the release agent is a metallic stearate—particularly calcium stearate. Generally speaking, the release agent is emulsified in the coagulant solution and is present at levels of about one percent by weight or less.

During processing of the nitrile-butadiene rubber glove according to the present invention, only one side of the layer of coagulated nitrile-butadiene latex forming the glove body on the glove former is subjected to halogenations (i.e., chlorination), if chlorination is used at all. That is, the glove body will have a chlorinated first surface forming a donning side of the glove body and an un-chlorinated second surface forming a grip side of the glove body. After forming, the glove is cured and vulcanized and may be rinsed multiple times to remove any excess coagulant and accelerators that may be present on or in the material.

Using the protocol described in ASTM D3767, procedure A, glove membrane thicknesses are measured. The elastomeric substrate can have an average thickness of about 0.025 or 0.03 mm to about 0.15 mm, typically from about 0.05 mm to about 0.13 mm, or from about 0.5 or 0.06 mm to about 0.08 or 0.10 mm. When made into a glove, according to certain embodiments, the substrate has a thickness in the palm region of about 0.05 mm to about 0.09 mm. More desirably, the substrate has a thickness in the palm region of about 0.05 mm to about 0.07 mm.

The gloves made using the current invention are less bulky and more pliable to wear, providing greater comfort compared to conventional nitrile-butadiene rubber gloves, and further can lead to cost savings in the manufacture process and ultimately to the consumer. With a thinner material, the wearer also enjoys greater tactile sensation in the hand and finger tips than compared with regular gloves.

Surface Features

Figure 1B:
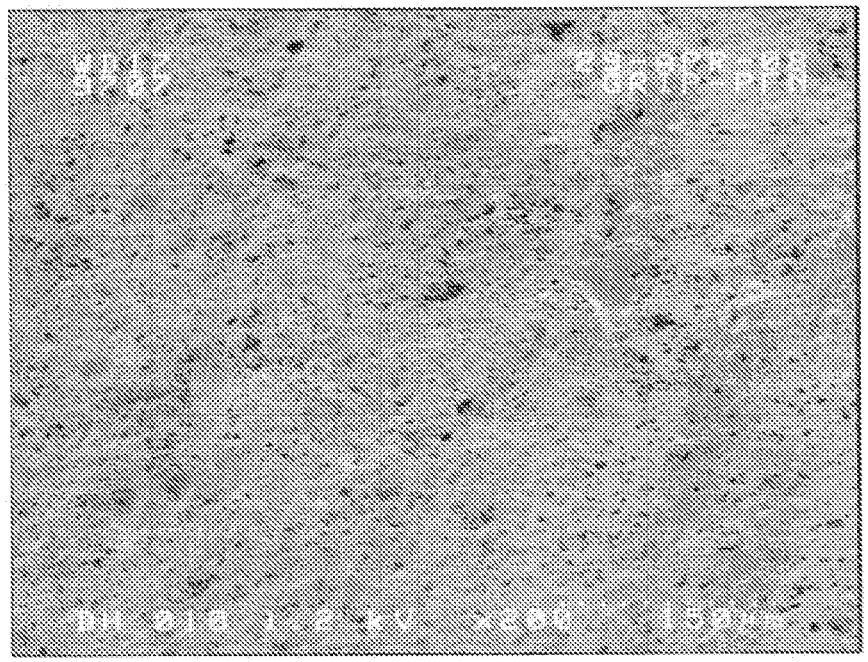

FIGS. 1A and 1B are scanning electron microscopy (SEM) photomicrographs, both at a linear magnification level of 200×, of the un-chlorinated outermost side of two different nitrile-butadiene rubber medical exam gloves. The side of the glove illustrated in the photomicrographs is the side adjacent the former during the dipping process and which becomes the outermost side as the glove is inverted when it is removed from the former. More particularly, the surface features of an exemplary elastomeric nitrile-butadiene rubber glove according to the present invention is illustrated in FIG. 1A. The exemplary elastomeric nitrile-butadiene rubber glove according to the present invention is occasionally referred to as a "Nitrile A" glove.

The surface features of an exemplary elastomeric medical exam glove illustrated in FIG. 1B are from a Kimberly-Clark® Safeskin® PURPLE Nitrile® medical exam glove available from Kimberly-Clark Corporation. The Kimberly-Clark® Safeskin® PURPLE Nitrile® medical exam glove may be referred to a "Nitrile C" glove.

As can be seen from these photomicrographs, the nitrile-butadiene rubber glove according to the present invention has greater surface "pitting" in the form of a distribution of small, numerous surface pores than the Kimberly-Clark® Safeskin® PURPLE Nitrile® medical exam glove.

Figure 2A:
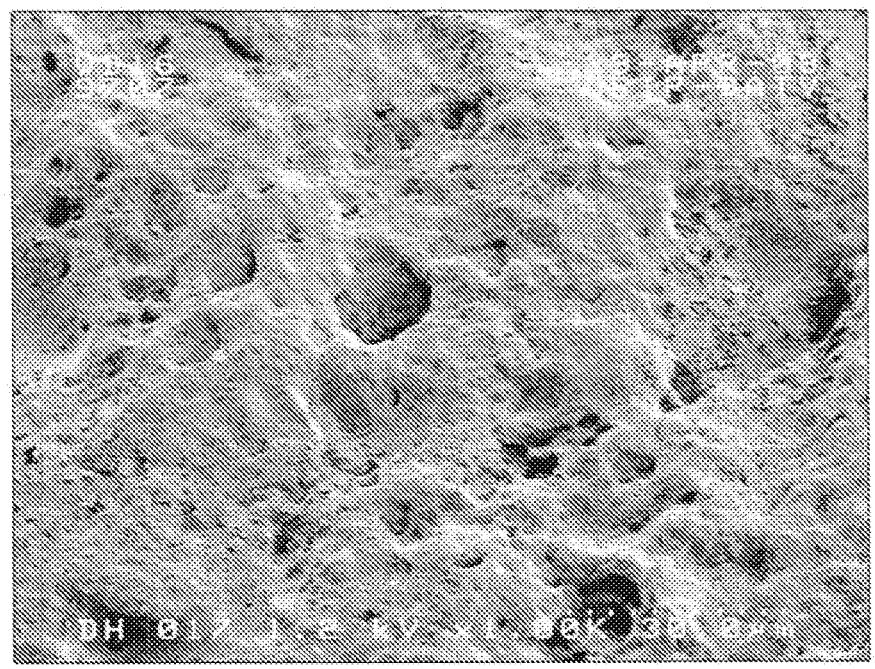
FIGS. 2A and 2B are scanning electron microscopy (SEM) photomicrographs, at a linear magnification level of 1000×.
Figure 2B:
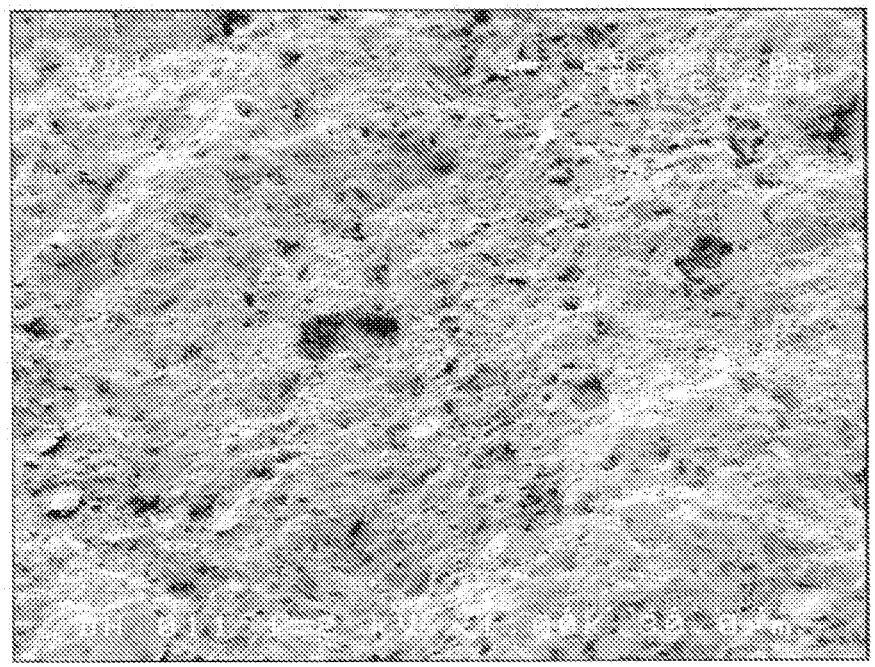

FIGS. 2A and 2B are scanning electron microscopy (SEM) photomicrographs, at a linear magnification level of 1000×. FIG. 2A illustrates the characteristics of an exemplary surface of an elastomeric glove according to the present invention. FIG. 2B illustrates the surface features of the Kimberly-Clark® Safeskin® PURPLE Nitrile® medical exam glove. As shown in these more detailed views of the surfaces of each glove, the nitrile-butadiene rubber glove according to the present invention has greater surface "pitting" in the form of a distribution of small, numerous surface pores than the Kimberly-Clark® Safeskin® PURPLE Nitrile® medical exam glove. These small, numerous surface pores do not appear to affect the water vapor transmission rate (WVTR) performance by increasing the increasing the WVTR performance. Moreover, the small, numerous surface pores do not adversely affect tactile perception. Generally speaking, the pores are "concave" and are essentially below the general level of the surface. At least for this reason, the small, numerous surface pores do not appear to be sensed by touch. To an ordinary wearer of a glove according to the present invention, the tactile sensation and texture of at least the un-chlorinated exterior or "grip side" glove is more "silky" or "smooth" than that of a conventionally manufactured nitrile rubber glove. The small, numerous surface pores appear to have little or no adverse effect regarding a tactile perception of roughness. That is, the surface pores as generally illustrated in FIG. 2A at least at the un-chlorinated exterior or "grip side" of the glove of the present invention are undetectable to an ordinary user and do not interfere with or degrade the generally "silky" or "smooth" tactile sensation experienced by a user in comparison to a similarly un-chlorinated exterior or "grip side" of a conventional nitrile-butadiene rubber glove.

The generally "silky" or "smooth" surface of at least the un-chlorinated exterior or "grip side" of the glove of the present invention can be characterized or expressed quantitatively by any number of ways known to those skilled in the art using well-known non-contact optical profilometry techniques. As an example, two-dimensional smoothness can be expressed in terms of the roughness average (Ra), the root mean square roughness (Rq), the maximum height of the profile (Rt), or the average maximum height of the profile (Rz).

Figure 3:
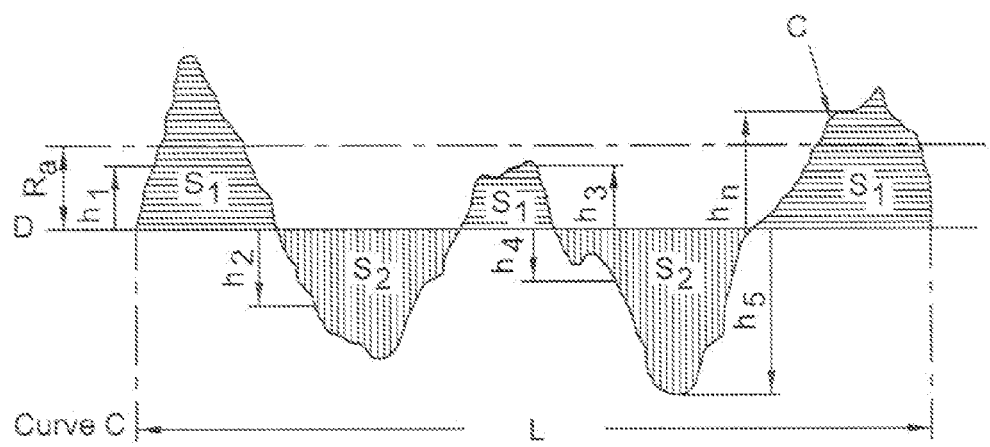
FIG. 3 is a schematic view illustrating an enlarged cross-section of an exemplary nitrile-butadiene rubber surface.

Although the gloves of the present invention are perceived as very smooth, on a microscopic level the surface features of the gloves have a surface texture, such as illustrated schematically and not necessarily to scale in FIG. 3, which represents an enlarged cross-section of an exemplary surface profile for a surface such as, for example, a surface of a glove.

Roughness Average is measured in micrometers and the Ra measurement for a sample length "L" is the mean height of the surface profile (peaks and inverted valleys). Smoother surfaces have fewer peaks and valleys or less variability in the heights or the peaks and/or the depths of the valleys. Referring again to FIG. 3, Curve "C" represents a two-dimensional profile of a section of a surface for a sample length "L". Line "D" is a representative line such that the sum of the surfaces S above and below line D is equal and is sometimes referred to as the mean line. Ra is the arithmetic average of the distances of height "h" of the curve "C" from the line "D". In other words, Ra is the mean height calculated over sample length.

Root Mean Square (RMS) roughness is designated as the parameter Rq. It is the root mean square average of the measured height deviations used in the calculation of Ra. Rq is more sensitive to large excursions from the mean line than Ra, which is an arithmetic average. If a surface has a profile that contains no large deviations from the mean surface level, the values of Ra and Rq will be similar. If there are appreciable numbers of large bumps or holes, the largest values of the profile height function will dominate the surface characteristics and Rq will be larger than Ra.

Rt is the maximum peak-to-valley height in the sampling length. Rz is the average of the greatest peak-to-valley separations and is known as the 10-point height parameter which is the average height difference between the five highest peaks and the five lowest valleys within the sampling length.

The roughness of the grip side surfaces of sample medical exam gloves were measured using non-contact optical profilometry techniques to create a three-dimensional representation of the surfaces as explained in further detail in the Experimental section of this document. Three-dimensional surface profilometry maps were exported from the profilometer for analysis with surface topography software as explained in further detail in the Experimental section of this document. The universal roughness parameters Sa (Surface Average Roughness) and Sq (Surface Root Mean Square Roughness) were calculated. The total z-envelope height (St) was also measured. St is not generally used or recognized as a measure of texture but is a simple dimensional indicator.

Sa (Surface Average Roughness) is the three-dimensional analogue of the two-dimensional roughness parameter Ra described above. Sq (Surface Root Mean Square Roughness) is the root mean square calculation which is more sensitive to larger deviations as generally explained above. Sq a dispersion parameter defined as the root mean square value of the surface departures within the three-dimensional sampling area and is sometimes referred to as the "Root-Mean-Square Deviation of the Surface" or the "Surface RMS Roughness". These roughness parameters are universally recognized and may be used to define differences.

Three-dimensional surface texture is composed of three components: roughness, waviness and form. With respect to the nitrile-butadiene gloves of the present invention, roughness is a function the fabrication process and includes surface irregularities that result from coagulation of the polymer latex and fabrication process. Waviness is the component that is superposed by roughness; and form is the overall shape of the surface minus contributions from roughness and waviness. See "Exploring Surface Texture" by H. Dagness (ISBN 0 901920 07 X) published by Rank Talylon Hobson Ltd., U.K. Data can be filtered using a waviness or roughness filter (essentially low and high pass filters) prior to calculation of roughness. Filters are selected based on what aspect of a surface is most important to measure (for example a speckle structure in a paint finish or longer wavelength ripples, etc.). The data reported herein were not filtered prior to calculation of Sa (Surface Average Roughness) and Sq (Surface Root Mean Square Roughness) since there was no basis to do so because the samples of glove materials were flat.

Table 1 below lists the results of the profilometric analysis for a sample un-chlorinated "grip-side" or exterior surface of a nitrile-butadiene rubber glove according to the present invention (referred to as the Nitrile A glove) and for a sample un-chlorinated "grip-side" or exterior surface of a Kimberly-Clark® Safeskin® PURPLE Nitrile® medical exam glove available from Kimberly-Clark Corporation (referred to as the Nitrile C glove). These three-dimensional roughness results are based solely on the analysis of the three-dimensional representation of the surfaces created by non-contact optical profilometry techniques.

TABLE 1

Comparative Summary of Surface Roughness

| Material type | Sample | Sa (μm) | Sq (μm) | St (μm) |
|---|---|---|---|---|
| Nitrile A | 1 | 2.04 | 3.63 | 60.6 |
|  | 2 | 2.17 | 4.32 | 63.0 |
|  | Average | 2.10 | 3.98 | 61.8 |

TABLE 1-continued

Comparative Summary of Surface Roughness

| Material type | Sample | Sa (μm) | Sq (μm) | St (μm) |
|---|---|---|---|---|
| Nitrile C | 1 | 4.67 | 10.6 | 69.0 |
|  | 2 | 3.20 | 7.51 | 66.8 |
|  | Average | 3.94 | 9.06 | 67.9 |
| Ratio Nitrile C/Nitrile A |  | 1.87 | 2.27 |  | units = micrometers (μm)
Sa = Surface Average Roughness
Sq = Surface Root Mean Square Roughness
St = z-envelope height The profilometric results indicate that the grip side of Nitrile A glove has significantly lower average roughness than the grip side of Nitrile C glove. As can be seen from the calculated "Ratio Nitrile C/Nitrile A" of the average of two samples, the grip side of the Nitrile C glove has a Surface Average Roughness (Sa) that is approximately 87% rougher than the grip side of the Nitrile A glove based. As can also be seen from the calculated "Ratio Nitrile C/Nitrile A" of the average of two samples, the Nitrile C glove has a Surface Root-Mean-Square Roughness (Sq) is 227% greater than of Nitrile A. These differences are believed to be meaningful such that the Nitrile A glove has a noticeably smoother surface that that is readily detected by an ordinary person who handles or uses the glove.

Generally speaking, the Surface RMS Roughness (Sq) of at least the un-chlorinated grip side of the gloves according to the present invention (i.e., Nitrile A gloves) may have a value ranging from about 3.00 μm to about 6.55 μm. Desirably, the Surface RMS Roughness (Sq) of at least the un-chlorinated grip side of the gloves according to the present invention (i.e., Nitrile A gloves) may have a value of less than about 5.20 or 5.30 μm. More desirably, the Surface RMS Roughness (Sq) of at least the un-chlorinated grip side of the gloves according to the present invention (i.e., Nitrile A gloves) may have a value of less than about 3.5 or 3.0 μm. In some embodiments, the Surface RMS Roughness (Sq) of at least the un-chlorinated grip side of the gloves according to the present invention (i.e., Nitrile A gloves) may have a value of below 2.0 μm or even lower. It is contemplated that Surface RMS Roughness (Sq) values may be as low as about 1.0 or 0.5 μm.

In addition to having at least an un-chlorinated grip side surface that may readily be characterized by non-contact optical profilometry analysis as smoother than other nitrile-butadiene rubber gloves, a glove made according to the present invention also has a distribution of larger and more numerous pores on at least an un-chlorinated grip side surface of the glove as generally illustrated in FIG. 2A. This distribution of larger and more numerous pores on at least an un-chlorinated grip side surface of the glove may readily be characterized by optical image analysis as explained in further detail in the Experimental section of this document. For the purposes of the present invention, the term "pore" or "pores" refers to small opening in the surface of a nitrile-butadiene glove surface that does not typically pass through the entire material of the glove.

As discussed above, these small, numerous surface pores do not appear to affect the water vapor transmission rate (WVTR) performance by increasing the increasing the WVTR performance. Moreover, the small, numerous surface pores do not adversely affect tactile perception. Generally speaking, the pores are "concave" and are essentially below the general level of the surface. At least for this reason, the small, numerous surface pores do not appear to be sensed by touch.

Generally speaking, it is believed that the release agent in the form of a waxy material that is coated on the glove form or glove mold, such as the stearate from a powder-free calcium stearate coagulant distributes itself with a relatively great uniformity on the surface of the glove. Evidence of this uniformity is that no build-up or other poor release effects are observed on the molds after significant use. As discussed above, the present invention provides a longer gelation time in which NBR latex particles are believed to react with the coagulant more efficiently and for a longer duration allowing more time for the latex particles to become more tightly packed together in the film layer. While the inventors should not be held to any particular theory of operation, the effect of the distribution of release agent on the nitrile-butadiene latex film layer is thought to work in combination with the longer gelation time and the more compact organization of the latex particles to result in a much smoother surface when a glove when a single layer of nitrile-butadiene rubber latex is formed on the mold in a single latex dip process, as well as to result in a distribution of larger and more numerous pores on at least an un-chlorinated grip side surface of the glove that may readily be characterized by optical image analysis.

Generally speaking, it is believed that the elastomeric nitrile-butadiene medical exam gloves of the present invention having a distribution of pores with an average diameter that is larger and more evenly spaced than other nitrile-butadiene medical exam gloves conveys an advantage in consistent flexibility and/or drape. The dimpled or discontinuous surface created by the pores, is thought to help enable the material to fold more easily. Further, this feature can be used to better retain surface active agents such as antimicrobial agents, fragrances, scents, or the like.

The un-chlorinated outer or "grip" surface of the glove body of the present invention has a pore density of greater than or equal to about 800 pores per $mm^2$ as determined by optical image analysis. That is, the number of a concave dimples or pits (generally referred to as "pores") located on the un-chlorinated outer (grip) surface of the glove body is greater than or equal to about 800 pores per $mm^2$ as determined by optical image analysis techniques. For example, the un-chlorinated outer or "grip" surface of the glove body may have a pore density ranging from about 820 per $mm^2$ to about 1600 per $mm^2$ as determined by optical image analysis. It is contemplated that the un-chlorinated outer or "grip" surface of the glove body may have a pore density greater than about 1600 per $mm^2$. In other examples, the un-chlorinated outer or "grip" surface of the glove body may have a pore density that ranges from about 850 per $mm^2$ to about 1450 per $mm^2$. In yet other examples, the un-chlorinated outer or "grip" surface of the glove body may have a pore density that ranges from about 900 per $mm^2$ to about 1280 per $mm^2$. In comparison, a similarly un-chlorinated exterior or "grip side" of a thicker nitrile-butadiene rubber glove such as, for example, a Kimberly-Clark® Safeskin® PURPLE Nitrile® medical exam glove typically has a pore density of less than 700 pores per $mm^2$ as determined by optical image analysis.

In a comparative measurement of a representative sample of the un-chlorinated outer or "grip" surface of the glove body of the present invention versus the un-chlorinated outer or "grip" surface of a representative thicker and more conventionally produced nitrile-butadiene rubber glove (i.e., a Kimberly-Clark® Safeskin® PURPLE Nitrile® medical exam glove), the glove of the present invention has a pore density of 1153 pores per $mm^2$, which is nearly twice (~1.71×) the pore density of the comparative glove surface at 673 pores per mm². The pores in the present substrate are generally more evenly distributed in a given area of the substrate surface than in the comparable surface (i.e., un-chlorinated outer or "grip" surface) of conventional nitrile-butadiene rubber gloves. The average pore size in the glove of the present invention is also about 16% larger than that in the comparable surface of conventional nitrile-butadiene rubber gloves. The gloves of the present invention have pores displaying an average "equivalent circular diameter" as determined by optical image analysis of between about 5 micrometers (μm) and about 6.5 micrometers (μm) in the present substrate, as compared to an average equivalent circular diameter of about 4.0 μm to about 5.6 μm in the comparable surface of conventional nitrile-butadiene rubber gloves.

Moisture Vapor Transmission Rate

Samples of three different types of nitrile-butadiene rubber gloves were tested to measure Water Vapor Transmission Rate as explained in more detail below in the Experimental section of this document. As used herein, the "Water Vapor Transmission Rate" (WVTR) generally refers to the rate at which water vapor permeates through a material as measured in units of grams per meter squared per 24 hours (g/m²/24 hrs) or (g/m²/day). The moisture vapor transmission rates of the three gloves were tested in accordance with ASTM Standard E96-80. Other techniques that are well-suited for materials thought to have a WVTR of up to about 3,000 grams per meter squared per 24 hours (g/m²/24 hrs) may be used, such as, for example the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which may be carried out utilizing, for example, a PERMATRAN-W Model 100K manufactured by Mocon/Modern Controls, Inc., Minneapolis, Minn.

The three different types of nitrile-butadiene rubber gloves were tested to measure Water Vapor Transmission Rate. The three different types of gloves are as follows:

(1) A nitrile-butadiene rubber glove according to the present invention which had a thickness in the palm region of the glove of approximately 0.05 millimeters as determined by ASTM D3767, procedure A (referred to as "Nitrile A glove" or just "Nitrile A"). This glove has an un-chlorinated grip side surface and is manufactured as discussed above using a powder-free coagulant and a release agent in the form of calcium stearate.

(2) A Kimberly-Clark® STERLING® nitrile medical exam glove (a nitrile-butadiene rubber glove which had a thickness in the palm region of the glove of approximately 0.08 millimeters as determined by ASTM D3767, procedure A (referred to as "Nitrile B glove" or just "Nitrile B"). This glove also has an un-chlorinated grip side surface and is manufactured as using a powder-free coagulant and a waxy release agent in the form of a metallic stearate.

(3) A Kimberly-Clark® Safeskin® PURPLE Nitrile® medical exam glove (a nitrile-butadiene rubber glove) available from Kimberly-Clark Corporation which had a thickness in the palm region of the glove of approximately 0.11 millimeters as determined by ASTM D3767, procedure A (referred to as "Nitrile C glove" or just "Nitrile C"). This glove also has an un-chlorinated grip side surface and is manufactured as using a powder-free coagulant and a waxy release agent in the form of a metallic stearate.

Figure 4:
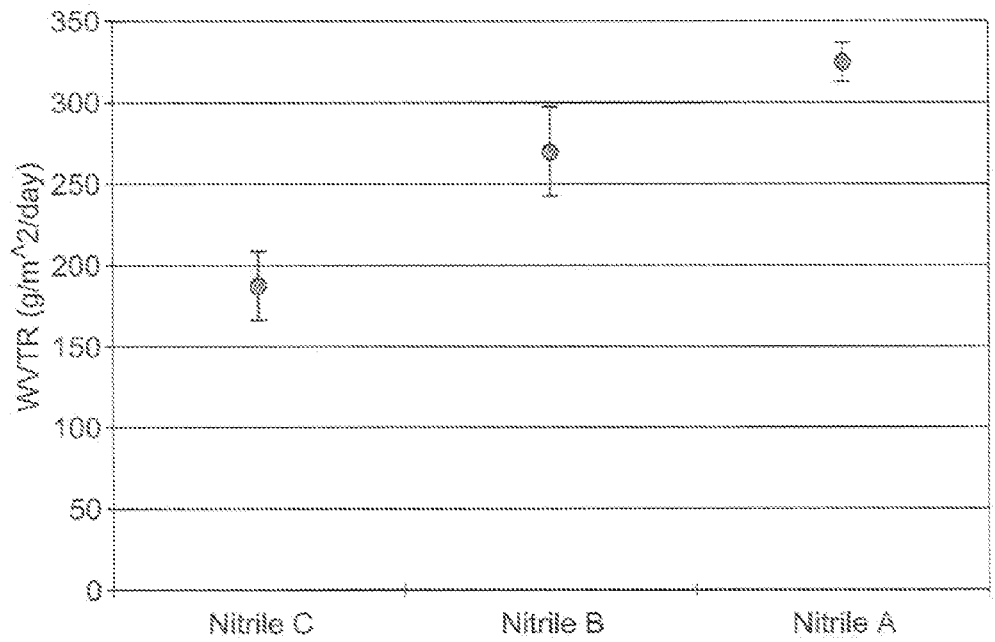
FIG. 4 is a graphical plot of water vapor transmission rate (WVTR) results for three different kinds of nitrile-butadiene rubber medical exam gloves.

The individual test results, along with the average and standard deviation for five sub-samples of each glove type are provided in Table 2A below. This data is shown graphically in FIG. 4, which is a graphical plot of water vapor transmission rate (WVTR) results for the three different kinds of nitrile-butadiene rubber gloves substrates identified above. As shown in Table 2A and in FIG. 4, the comparative nitrile-butadiene rubber gloves (i.e., Nitrile B glove and Nitrile C glove) have an average Water-Vapor Transmission Rate (WVTR) of less than about 250 or 275 g/m²/day. The thin, nitrile-butadiene gloves according to the present invention (i.e., the Nitrile A gloves) exhibit an average Water-Vapor Transmission Rate (WVTR) of more than at least about 285 g/m²/day and may exhibit values of up to about 550 g/m²/day. According to the present invention, the average WVTR for Nitrile A gloves generally is at least about 300 g/m²/day, and may exhibit values of up to about 460 or 480 g/m²/day. The WVTR for Nitrile A glove samples may have an average WVTR between about 310 or 315 g/m²/day to about 400 or 430 g/m²/day. According to certain samples, the average WVTR may range from about 317±3 g/m²/day to about 345±3 g/m²/day.

TABLE 2A

WVTRs for Three Nitrile-butadiene rubber glove Types

| Sample | ASTM 2437 Water Vapor Transmission Rate (g/m²/day) | | |
|---|---|---|---|
| | Nitrile A | Nitrile B | Nitrile C |
| 1 | 338 | 280 | 179 |
| 2 | 316 | 278 | 182 |
| 3 | 342 | 242 | 203 |
| 4 | 329 | 247 | 213 |
| 5 | 316 | 263 | 161 |
| Avg. | 328.2 | 262.0 | 187.6 |
| Std Dev | 11 | 28 | 21 |

From Table 2A, one can see that Nitrile A gloves have the highest average WVTR and are considered the most "breathable" of the three glove types tested. Generally speaking, when an ordinary user wears the Nitrile A continuously for any length of time, particularly for more than about 5 minutes, the Nitrile A gloves tend to feel cooler than comparative nitrile-butadiene rubber gloves. This feeling of coolness is readily noticeable to ordinary users through their unaided sensation of skin surfaces of their hand that are covered by the glove.

The Water-Vapor Transmission Rate (WVTR) is a phenomenon that is influenced or impacted by many variables, including the thickness of the material through which water vapor must pass. If all conditions are generally similar, the WVTR would be expected to be relatively predictable and proportional for similar materials having different thicknesses. In this case, the nitrile-butadiene rubber material of the three different gloves are considered to be generally similar materials (i.e., all are medical exam glove grade nitrile-butadiene rubber formed from nitrile-butadiene rubber latex) and one of ordinary skill would expect the WVTR for the Nitrile A glove and the Nitrile B glove to be predictable based on the WVTR performance of the Nitrile C glove.

Figure 9:
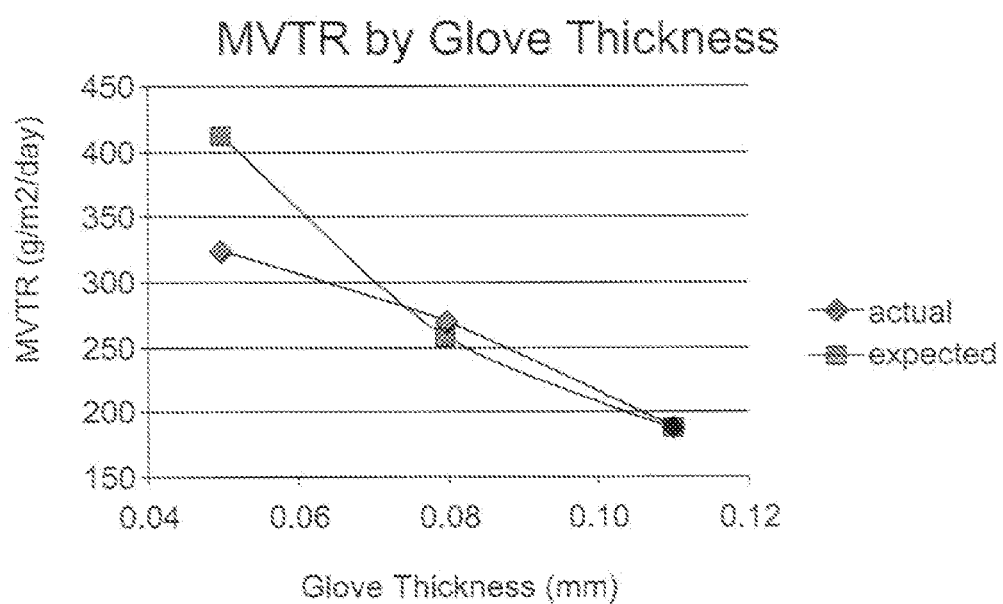
FIG. 9 is a graph illustrating exemplary relationships between glove thickness and Water Vapor Transmission Rate for various sample nitrile-butadiene rubber medical exam gloves.

The WVTR performance for the Nitrile A glove and the Nitrile B glove may be predicted from the actual WVTR performance of the Nitrile C glove and the relative thicknesses of the Nitrile C glove and the Nitrile A glove or Nitrile B glove. For example, for the Nitrile B glove, this was accomplished by the following formula:

Nitrile $B$ WVTR=[Nitrile $C$ thickness(mm)/Nitrile $B$ thickness(mm)]×Nitrile $C$ WVTR Table 2B summarizes the WVTR data for the three type of nitrile material, as above, as actually observed and as predicted from the Nitrile C glove. FIG. 9 presents the data in graphical form.

TABLE 2B

WVTR for Three Nitrile-Butadiene Rubber Glove Types

| Sample Glove | Thickness (mm) | WVTR actual (g/m$^2$/day) | WVTR Predicted (g/m$^2$/day) |
|---|---|---|---|
| Nitrile A | 0.05 | 324 | 411 |
| Nitrile B | 0.08 | 262 | 257 |
| Nitrile C | 0.11 | 187 | — |

As shown in Table 2B, the WVTR for a glove made according to the present invention is less than proportional to its thickness in comparison to the other nitrile-butadiene rubber gloves. For example, a comparison of the actual WVTR for the Nitrile A glove with its predicted WVTR (calculated from the thickness and actual WVTR of the Nitrile C glove) reveals that the actual WVTR for Nitrile A glove is about 23% less than predicted—based on glove thickness.

Table 2C summarizes the WVTR data for the three type of nitrile material, as above, as actually observed and as predicted from the Nitrile B glove.

TABLE 2C

WVTR for Three Nitrile-Butadiene Rubber Glove Types

| Sample Glove | Thickness (mm) | WVTR actual (g/m$^2$/day) | WVTR Predicted (g/m$^2$/day) |
|---|---|---|---|
| Nitrile A | 0.05 | 324 | 419 |
| Nitrile B | 0.08 | 262 | — |
| Nitrile C | 0.11 | 187 | 191 |

A comparison of the actual WVTR for the Nitrile A glove with its predicted WVTR (calculated from the thickness and actual WVTR of the Nitrile B glove) reveals that the actual WVTR for Nitrile A glove is about 25% less than predicted—based on glove thickness.

In other words, the WVTR is not linearly proportional based on thickness alone, and the material does not have a constant standardized WVTR. While the inventors should not be held to a particular theory of operation, the nitrile rubber medical exam gloves according to the present invention appear to have about 20% denser structure per unit volume than one would usually expect from a mere decrease in thickness of a comparable elastomeric film or membrane. As used here, "density" refers not to bulk density as is more common, but rather refers to molecular density or order. It is believed that the nitrile-butadiene rubber gloves of the present invention have a more highly ordered molecular structure than other nitrile-butadiene rubber gloves. Not intending to be bound by theory, this is evidenced by the fact that the WVTR for a glove made according to the present invention is less than proportional to its thickness, compared to other nitrile-butadiene rubber gloves. In other words, the WVTR is not linearly proportional based on thickness alone, and the material does not have a constant standardized WVTR. This may indicate a more finely ordered or denser structure. The more tightly packed structure may contribute to the topographical features of the elastomeric film membrane that we have observed.

Generally speaking, the nitrile-butadiene rubber medical exam gloves of the present invention exhibit Water Vapor Transmission Rates that are comparable to the thinnest commercially available polyvinyl chloride medical exam gloves, which may have WVTR values of about 350 g/m$^2$/24 hr day. However, most polyvinyl chloride medical exam gloves have WVTR values that are lower.

Physical Properties

For elastic materials such as elastomeric medical exam gloves, force-strain properties refer to a direct measurement of how a material elastically deforms or responds (i.e., stretches) in response to an applied force, regardless of the thickness of the material. The results of force strain testing are reported in units of force (e.g., Newtons or pounds-force) at a specified distance. Force-strain properties are frequently referred to as "force-to-stretch".

For elastic materials such as elastomeric medical exam gloves, stress-strain properties measure the response to an applied force per unit cross sectional area of the material. This property, sometimes referred to as "modulus", has dimensions of Force/Area and is measured in units such as the Pascal or in units such as Newton per square meter (1 Pa=1 N/m$^2$), dyne/cm$^2$, or pounds-force per inch squared (psi).

As used herein, the term "stretch-elongation" refers to the amount or percentage that an elastomeric substrate or membrane is stretched or expanded exceeding its original dimensions. The "percentage deformation" or "percentage elongation" can be determined according to the following calculation:

Percentage Elongation=[(Final dimension−Initial dimension)/Initial dimension]×100

Similar to the nitrile-butadiene rubber materials described in U.S. Patent Publication Nos. 2006/0253956 (A1), and 2006/0257674 (A1), the contents of which are incorporated herein by reference, the flexibility and "softness" of an elastic membrane can be characterized by its force-to-strain value. For purposes of the present invention, the testing and performance of elastic medical exam gloves will be reported in terms of force-strain or "force-to-stretch" properties. The force-strain or "force-to-stretch" properties relate more directly to actual conditions of the medical exam gloves. The force-strain or "force-to-stretch" properties at a given thickness are particularly important for thin gloves to have a comfortable force response because nitrile-butadiene rubber formulations designed for thin gloves to have sufficient strength and barrier properties can result in a stiffer and less comfortable glove.

It is believe that softer and more flexible material is important for a medical exam glove to provide comfort provided the glove also exhibits satisfactory levels of barrier performance. The nitrile-butadiene medical exam gloves of the present invention have force-to-stretch to a given extension that compare favorably with medical exam gloves formed from natural rubber latex. The nitrile-butadiene medical exam gloves of the present invention have more comfortable levels of force-to-stretch to a given extension, particularly in comparison to conventional polyvinyl chloride medical exam gloves and thicker nitrile-butadiene medical exam gloves, as will be further illustrated below while also exhibiting satisfactory levels of barrier performance in comparison to thicker nitrile-butadiene medical exam gloves and superior levels of barrier performance in comparison to polyvinyl chloride medical exam gloves as illustrated by pinhole defect testing. Importantly, the present invention provides these performance advantages in a practical and economical way to combine the economic advantages of an inexpensive polyvinyl chloride medical exam glove with a level of force-to-stretch performance and barrier performance that compares favorably with more expensive and conventionally thicker nitrile-butadiene medical exam gloves.

Figure 5:
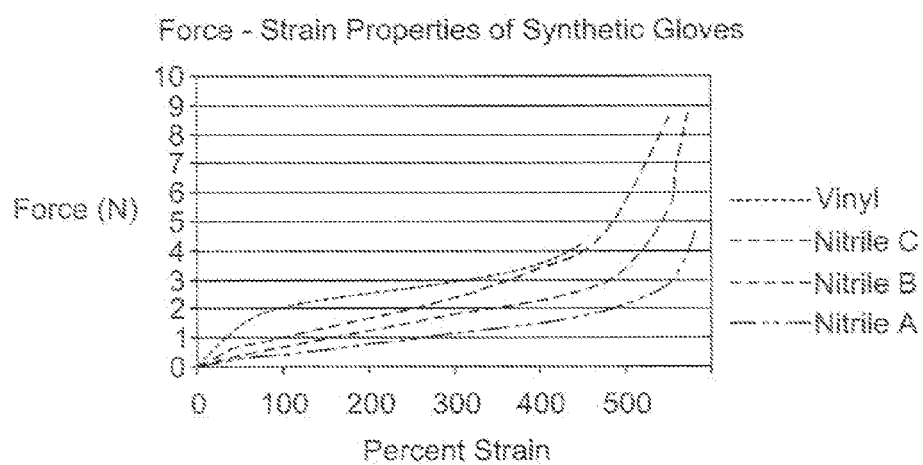
FIG. 5 is a comparative graph of the Force-Strain properties from four different medical exam gloves made from synthetic materials.

FIG. 5 is a comparative graph of the Force-Strain properties from four different samples of medical exam gloves made from synthetic materials.

One substrate is a conventional polyvinyl chloride medical exam glove available as the Universal™ 3 G Powder-Free Stretch Synthetic Exam Glove from Medline Industries, Inc. of Mundelein, Ill., (referred to as "Vinyl") and three other substrates are: (1) a nitrile-butadiene rubber glove according to the present invention which had a thickness in the palm region of the glove of approximately 0.05 millimeters as determined by ASTM D3767, procedure A (referred to as "Nitrile A glove" or just "Nitrile A"); (2) a Kimberly-Clark® STERLING® nitrile medical exam glove (a nitrile-butadiene rubber glove which had a thickness in the palm region of the glove of approximately 0.08 millimeters as determined by ASTM D3767, procedure A (referred to as "Nitrile B glove" or just "Nitrile B"); and (3) a Kimberly-Clark® Safeskin® PURPLE Nitrile® medical exam glove (a nitrile-butadiene rubber glove) available from Kimberly-Clark Corporation which had a thickness in the palm region of the glove of approximately 0.11 millimeters as determined by ASTM D3767, procedure A (referred to as "Nitrile C glove" or just "Nitrile C").

A comparison of the relative amounts of applied force (Newtons) necessary to stretch these nitrile rubber and vinyl-based gloves to 300% of an initial un-stretched dimension (length-wise) (F-300) is presented in Table 3. Typical polyvinyl chloride medical exam gloves have a thickness in the palm region of about 0.13-0.16 mm, and an applied force at break of about 3.5-4.5 N, at a maximum strain of about 440% elongation. The nitrile-butadiene rubber glove according to the present invention (Nitrile A glove) requires only an applied force of less than or equal to about 1.5 N at about 300% strain and less than about 2 N at about 400% strain, or about 2 N at about 500% strain. The amount of force to stretch an elastic substrate sample, Nitrile A, with a thickness ranging from about 0.03 mm to about 0.10 mm (more desirably, a thickness ranging from about 0.05 mm to about 0.08 mm, and still more desirably, a thickness ranging from about 0.055 to about 0.08 mm) ranges from about 1.08 N to about 1.45 N, with an average value of about 1.12 N at about 0.07 mm.

The nitrile-butadiene medical exam gloves identified as the Nitrile B glove and the Nitrile C glove, show a more pronounced difference. The average amount of force applied to stretch 300% of an initial dimension (F-300) for the Nitrile B glove is about 1.77 N, and the average amount of force applied to stretch 300% of an initial dimension (F-300) for the Nitrile C glove is about 2.47 N. For sake of comparison, a polyvinyl chloride medical exam glove of similar thickness (~0.08 mm) is more resistant to stretching than either of the other nitrile-butadiene rubber glove samples. The Universal™ 3 G Powder-Free Stretch Synthetic Exam Glove (i.e., Vinyl) requires an average F-300 of about 2.92 N—the most force to stretch—almost three times the force required for the Nitrile A glove—the glove according to the present invention.

TABLE 3

Average Force to Stretch a Substrate to 300% of Initial Dimensions (F-300)

| Sample | Average Thickness (mm) | Average F-300 (Newtons) | F-300 Range (Newtons) |
|---|---|---|---|
| Nitrile A | 0.075 mm | 1.12 N | 1.06 N-1.48 N |
| Nitrile B | 0.080 mm | 1.77 N | 1.56 N-2.20 N |
| Nitrile C | 0.113 mm | 2.47 N | 2.25 N-2.65 N |
| Vinyl | 0.130 mm | 2.92 N | 2.80 N-3.10 N |

The medical exam glove of the present invention may a force-strain response of a force (F300) of less than or equal to about 1.50 N at about 300% strain. Typically, according to the invention, the medical exam glove exhibits a force-response behavior that requires a force of no more than about 1.45 N to stretch a test sample of the medical exam glove with a thickness of about 0.03-0.10 mm to about 300% of an initial, un-stretched dimension. Further, the medical exam glove exhibits a force-strain response of a force of less than about 2 N at about 400% strain, or about 2 N at about 500% strain. An elastomeric glove according to the present invention having a thickness of between about 0.05 to 0.10 mm in the palm region, desirably exhibits a force to break of less than 6.0 N or 6.5 N (desirably about 4N to about 6N), at an elongation at break of about 560 to about 630% of its original un-stretched dimension. An elastomeric glove according to the present invention having a thickness of between about 0.05 to 0.10 mm in the palm region, desirably exhibits a force to break of less than 6.0 N or 6.5 N, at an elongation at break of about 600 to about 630% of its original un-stretched dimension.

A range of other physical properties were determined for various commercially available polyvinyl chloride medical exam gloves, for a commercially available nitrile-butadiene rubber medical exam glove, and for an exemplary medical exam glove prepared in accordance with the present invention. The gloves are as follows:

Vinyl 1: MediGuard Vinyl Synthetic Powder-Free Exam Gloves available from Medline Industries, Inc. of Mundelein, Ill.

Vinyl 2: Mediline Aloetouch® 3 G Powder-Free Synthetic Exam Gloves available from Medline Industries, Inc. of Mundelein, Ill.

Vinyl 3: Universal™ 3 G Powder-Free Stretch Synthetic Exam Glove available from Medline Industries, Inc. of Mundelein, Ill.

Vinyl 4: Mediline Aloetouch® Ultra IC Powder-Free Stretch Synthetic Coated Exam Gloves available from Medline Industries, Inc. of Mundelein, Ill.

Vinyl 5: Cardinal Health Esteem® Stretchy Synthetic Powder-Free Vinyl Exam Gloves available from Cardinal Health of Dublin, Ohio.

Vinyl 6: Cardinal Health InstaGard® PV Powdered Vinyl Exam Gloves available from Cardinal Health of Dublin, Ohio.

Nitrile A: nitrile-butadiene rubber medical exam glove according to the present invention Nitrile B: Kimberly-Clark® STERLING® nitrile medical exam glove available from Kimberly-Clark Corporation, Roswell, Ga. (a nitrile-butadiene rubber glove referred to as "Nitrile B glove" or just "Nitrile B")

The elongation at break and force at break properties were determined in accordance with ASTM D412-06 utilizing the Die-D set of dimensions (Width dimension of the dumbbell specimen being 3 mm) using a sample size of 10 gloves. The thickness of the glove (i.e., the single glove membrane at the specified location) was determined in accordance with ASTM D3767 for a sample size of 10 gloves. The weight of the glove and the glove length, width at cuff and palm width was determined using conventional techniques for a sample size of 10 gloves. The results of testing are reported in Table 4 below:

TABLE 4

Comparative Properties of Polyvinyl Chloride Medical Exam Gloves

| TESTING | VINYL 1 | VINYL 2 | VINYL 3 | VINYL 4 | VINYL 5 | VINYL 6 | NITRILE A | NITRILE B |
|---|---|---|---|---|---|---|---|---|
| Elongation at break (%) | 443 | 445.3 | 447.4 | 506.4 | 421.1 | 357.1 | 582.8 | 577.2 |
| Force at break (N) | 4.749 | 4.335 | 5.02 | 5.224 | 6.055 | 5.074 | 4.338 | 7.935 |
| Finger Thickness (mm) | 0.121 | 0.097 | 0.123 | 0.129 | 0.135 | 0.104 | 0.08 | 0.1 |
| Palm Thickness (mm) | 0.098 | 0.088 | 0.09 | 0.1 | 0.095 | 0.105 | 0.06 | 0.071 |
| Cuff Thickness (mm) | 0.054 | 0.062 | 0.065 | 0.097 | 0.058 | 0.073 | 0.05 | 0.065 |
| Weight of glove (g) | 5.919 | 6.0108 | 6.5396 | 6.6011 | 6.395 | 6.4647 | 3.084 | 4.089 |
| Length of glove (mm) | 249 | 247.1 | 248.7 | 239.5 | 240.2 | 232.3 | 239.8 | 237.3 |
| Width at cuff (mm) | 89.2 | 91.1 | 90.5 | 91 | 89.8 | 97.8 | 87.4 | 90.8 |
| Palm width (mm) | 95.4 | 97 | 97.3 | 98.6 | 98.1 | 95.4 | 96.2 | 95.5 |

Pinhole defect testing of nitrile-butadiene rubber medical exam gloves according to the present invention was conducted generally in accordance with ASTM D5151-06 which is a "pass-fail" static water load test procedure. Sample of gloves in lot sizes of about 100 gloves were tested. The accumulated totals of gloves tested exceeded several thousand gloves (in some cases, several tens of thousands of gloves). The elastomeric glove according to the present invention had a failure rate of less than about 0.1 percent. In other words, less than 1 out 1000 gloves exhibited a pinhole defect when subjected to pinhole defect testing. The medical exam gloves of the present invention had a palm thickness as determined in accordance with ASTM D3767 averaging approximately 0.053 mm.

Several commercially available nitrile-butadiene rubber medical exam gloves were also tested generally in accordance with ASTM D5151-06 which is a "pass-fail" static water load test procedure. The palm thickness of the gloves is determined in accordance with ASTM D3767 and an average was determined. The identity of the glove, the number of sample gloves tested, the average palm thickness and the pinhole defect rate is reported below.

(1) Cardinal Esteem® Stretchy Nitrile powder-free medical exam available from Cardinal Health of Dublin, Ohio, average palm thickness: 0.13 mm, pinhole defect rate: 0.5%, 200 gloves tested.

(2) Medline Sensicare® Silk Nitrile powder-free medical exam glove available from Medline Industries, Inc. of Mundelein, Ill., palm thickness: 0.08 mm, pinhole defect rate: 3.8%, 600 gloves tested.

(3) Microflex UltraSense® Nitrile powder-free medical exam glove available from Microflex Corporation of Reno, Nev., palm thickness: 0.09 mm, pinhole defect rate: 0.3%, 300 gloves tested.

(4) Sempermed Sempercare® Tender Touch Nitrile powder-free medical exam glove available from Sempermed USA, Inc. of Clearwater, Fla., palm thickness: 0.09 mm, pinhole defect rate: 2.3%, 1292 gloves tested.

(5) Medgluv Neutron Grey Nitrile powder-free medical exam glove available from Medgluv, Inc. of Miami, Fla., palm thickness: 0.07 mm, pinhole defect rate: 2.45%, 489 gloves tested.

These results show that commercially available powder-free nitrile-butadiene rubber medical exam gloves that are substantially thicker than the gloves of the present invention have a significantly greater pinhole defect rate. For example, the lowest pinhole defect rate of 0.3 percent is provided by a glove having an average palm thickness of 0.09 mm that is approximately seventy percent (70%) greater than the palm thickness of the glove of the present invention having a palm thickness of about 0.053 mm.

In certain embodiments, one may treat or coat the elastomeric substrate (e.g., either the inner donning surface or outer (grip) side of a glove according to the present invention) with an antiseptic agent or odorant, such as citric acid, linalool, or lavender oil. Other nature or synthetic scented extracts (e.g., lavender scent) may also be applied to the substrate surface. The antiseptic agent may collect within the numerous pores of the elastic film for slow release over time. The pores retard the antiseptic agent or odorant from being wiped off in use and increase the likelihood that the active agent is retained. The concentrations of antiseptic or scent agents may range from about 0.001 gram/cm$^2$ up to about 0.80 gram/cm$^2$. Typically, the amounts may range from about 0.005 gram/cm$^2$ to 0.15 gram/cm$^2$; more typically from about 0.01 gram/cm$^2$ to about 0.05 or 0.07 gram/cm$^2$, inclusive.

Section—Experimental

I. Scanning Electron Microscopy (SEM) Imaging:

A small piece that was larger than about 1 millimeter squared (mm$^2$) was carefully removed from the grip sides of each glove and placed on the aluminum mounts using double-sided tape. The samples were mildly sputter coated with gold to render electrical conductivity, then imaged in a JEOL JSM 6490LV scanning electron microscope. Two images were acquired of each sample at 130× magnification which yields an area about 1 millimeter squared (mm$^2$), which is approximately the same area as scanned by the profilometer in the Non-Contact Profilometry analysis below. The images were taken using shadow mode backscatter imaging to clearly contrast the pores from the surface. These images were analyzed to obtain the average pore size and surface area percent coverage.

II. Non-Contact Profilometry:

Pieces of the grip sides were fixed to glass microscope slides using smooth double sided adhesive. The glove material was flattened onto the adhesive using mild pressure applied with a glass microscope cover slip. Optical scans were obtained using the FRT MicroProf® Optical Profilometer using a 100-micrometer z-range white-light sensor which has vertical resolution better than 10-nanometers and X-Y resolution of approximately 1 to 2 micrometers. The instrument is manufactured by Fries Research & Technology, GmbH, having an office at Friedrich-Ebert Strasse, 51429 Bergisch Gladbach, Germany Two different 1 mm×1 mm areas were scanned with a sampling density of 200 lines×200 points/line, giving data spacing of 5 micrometers in the X and Y dimensions yielding approximately 40,000 data points for each 1 mm×1 mm sample. The areas were pre-examined in a stereomicroscope to insure that the surfaces appeared typical and were free of defects or contaminant particles. The sample is fixed to the computer controlled XY stage which is scanned under the fixed optical sensor. The height at each point is calculated based on the measured wavelength of the reflections.

The data were converted to Surface Data Format (.sdf) and analyzed using Mountains 2.2 programming. The universal roughness parameters Sa and Sq were calculated and averaged. The total z-envelope height (St) was also measured. St is not generally used or recognized as a measure of texture but is a simple dimensional indicator.

Sa is the three-dimensional analogue of the 2D roughness parameter Ra, defined as the arithmetic average of the absolute values of the measured deviations about the least-squares best fit plane through the data. Sq is the RMS calculation, which is more sensitive to larger deviations. These roughness parameters are universally recognized and may be used to define differences.

III. Image Analysis and Moisture Vapor Transmission Rate:

Photomicrographs of the un-chlorinated grip-side surfaces of the Nitrile A glove and the Nitrile C glove were made using the JEOL JSM 6490LV scanning electron microscope (SEM) at a linear magnification of 130×. The SEM photomicrograph images were analyzed using the Leica Microsystems QWIN Pro version 3.2.1 image analysis software (available from Leica Microsystems of Heerbrugg, Switzerland) and the custom written Quantimet User Interactive Programming System (QUIPS) algorithm reproduced below:

```
CONDITIONS = Jeol JSM 6490 SEM
SET-UP & ACQUIRE IMAGE
Calibration  (Local)
Enter Results Header
File Results Header  (channel #1)
File Line  (channel #1)
Image frame  (x 0, y 0, Width 1280, Height 960)
Measure frame  (x 33, y 47, Width 1215, Height 824)
For  (FIELD = 1 to 2, step 1)
PIN DETECTION AND IMAGE PROCESSING
Read image [PAUSE] (from file C:)
Grey Transform  (BSmooth from Image0 to Image1, cycles 1, operator Disc)
Detect (blacker than 64, from Image1 into Binary0 delineated)
Binary Amend  (Open from Binary0 to Binary1, cycles 1, operator Disc, edge erode on)
Binary Amend  (Close from Binary1 to Binary2, cycles 2, operator Disc, edge erode on)
Binary Amend  (Open from Binary2 to Binary3, cycles 1, operator Disc, edge erode on)
Binary Identify  (FillHoles from Binary3 to Binary4)
MEASURE PIN AREA AND NUMBER (FIELD)
Measure field  (plane Binary4)
   Selected parameters:   Count, Area %
File Field Results  (channel #1)
File Line  (channel #1)
File Line  (channel #1)
MEASURE PIN SIZE DISTRIBUTION (FEATURE)
Measure feature  (plane Binary4, 8 ferets, minimum area: 10, grey image: Image0)
   Selected parameters: X FCP, Y FCP, Roundness, EquivDiam
Feature Histogram #1  (Y Param Number, X Param EquivDiam, from 1. to 100.,
   logarithmic, 25 bins)
Feature Histogram #2 (Y Param Number, X Param Roundness, from 1. to 3.5, linear, 25 bins)
Display Feature Histogram Results  (#1, horizontal, differential, bins + graph (Y axis linear), statistics)
   Data Window (1087, 801, 512, 359)
Next  (FIELD)
File Feature Histogram Results  (#1, differential, statistics, bin details, channel #1)
File Line  (channel #1)
File Line  (channel #1)
File Feature Histogram Results  (#2, differential, statistics, bin details, channel #1)
File Line  (channel #1)
File Line  (channel #1)
Close File  (channel #1)
END
```

Two images were analyzed per code and the measurement region size of each was 0.6 mm$^2$. Spatial calibration for the image analysis was performed using the QWIN Pro system software and the micron bar located on the SEM images.

The QUIPS algorithm was used to read the digital SEM images, automatically detect the pore regions, perform image processing on the detected binary regions, perform sizing measurements and export the data, in the form of a histogram, directly to an EXCEL® spreadsheet. Data from each of the two images analyzed per code were accumulated into a single equivalent-circular diameter (ECD) histogram.

Results showed that the Nitrile A glove sample had larger size pores as measured by equivalent-circular diameter (ECD) as well as over twice the percentage of pore surface area relative to the Nitrile C glove sample.

Figure 6A:
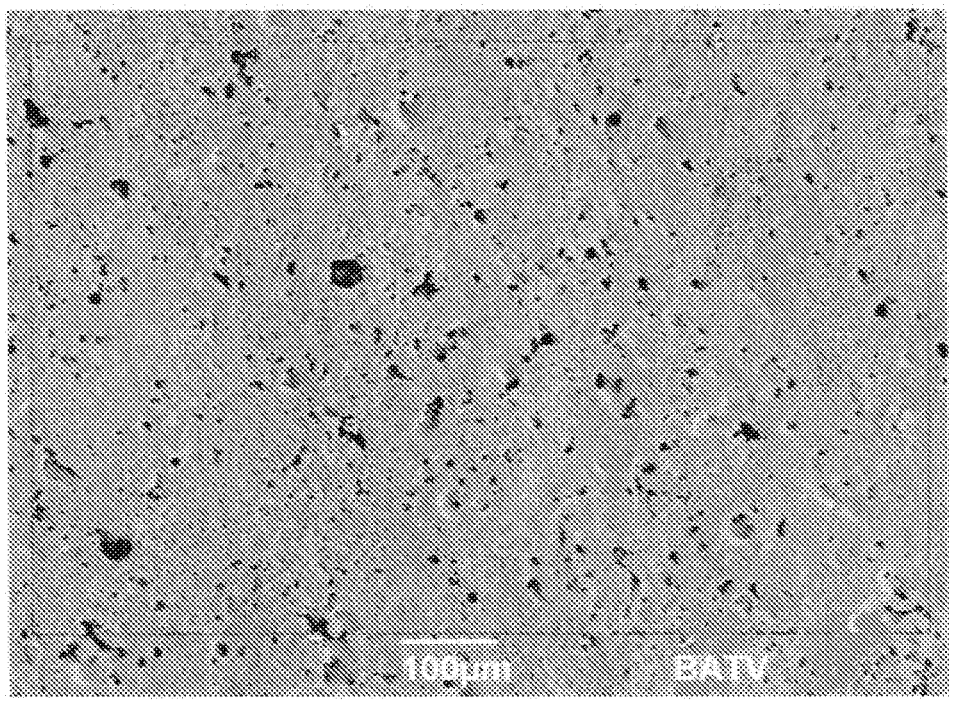
FIGS. 6A and 6B are scanning electron microscopy (SEM) photomicrographs, showing 'raw' and 'detected' pitting, respectively, for an exemplary surface of an nitrile-butadiene rubber medical exam glove according to the present invention.
Figure 6B:
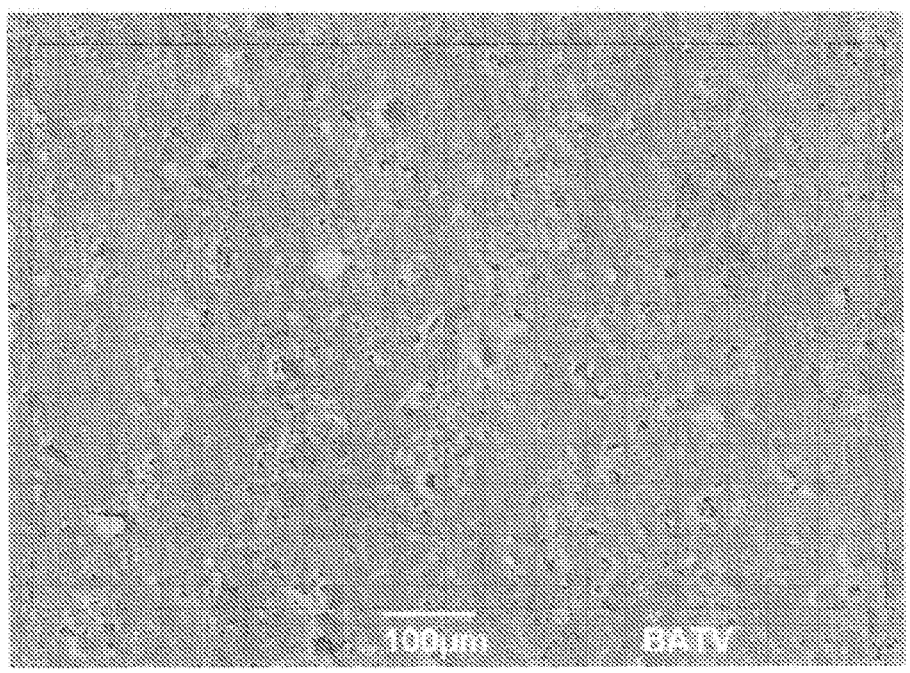
Figure 7A:
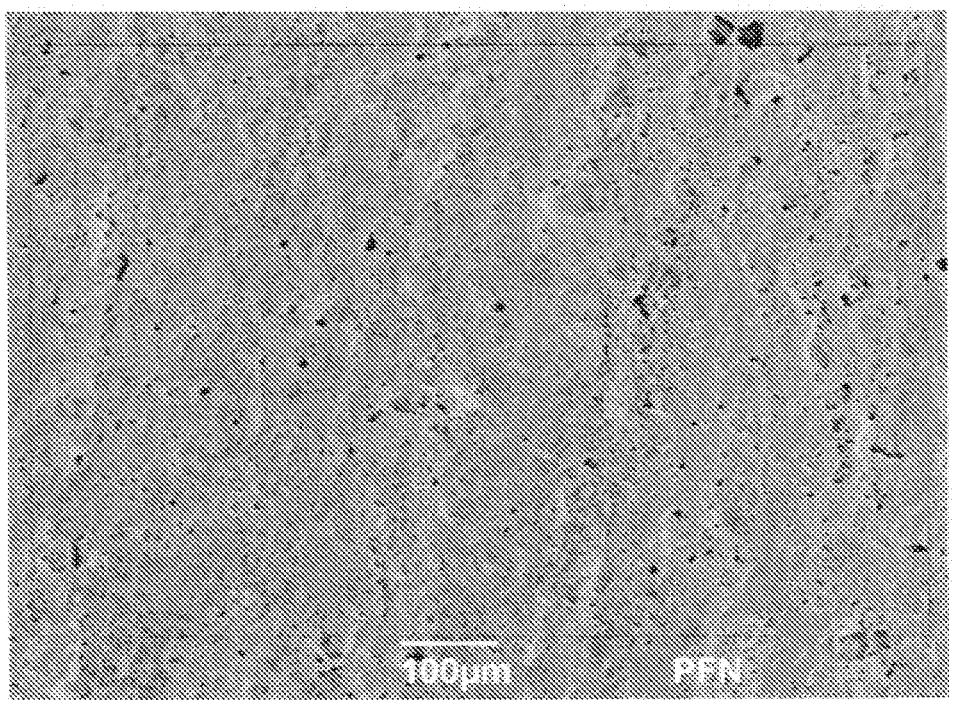
FIGS. 7A and 7B are representative images showing 'raw' and 'detected' pitting, respectively, for an exemplary surface of a comparative, commercially-available nitrile-butadiene rubber medical exam glove.
Figure 7B:
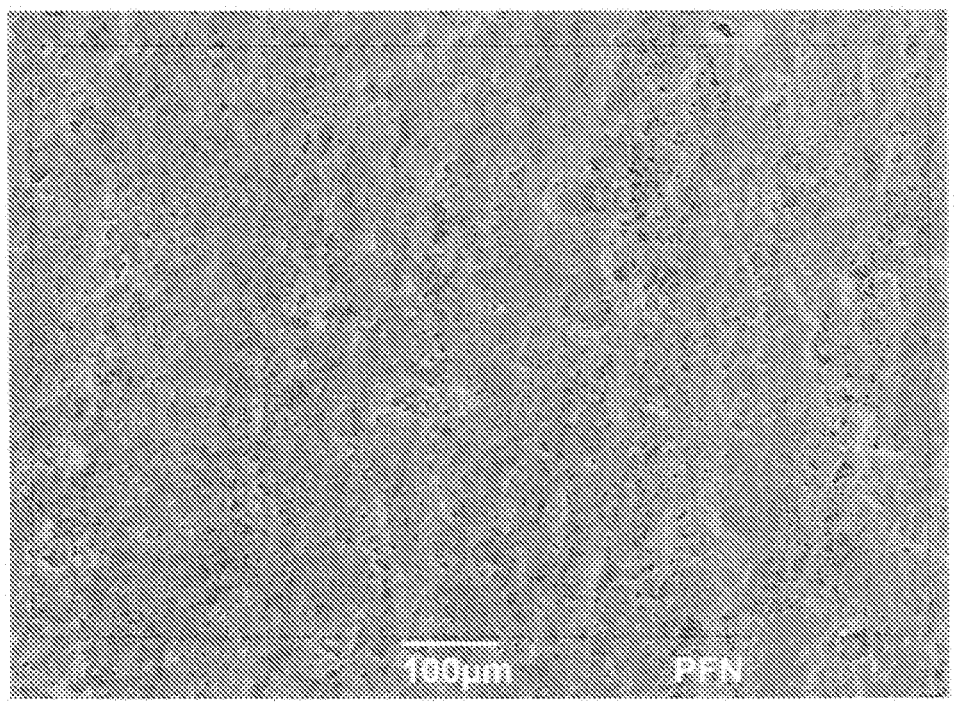

Photomicrograph images acquired using the JEOL JSM 6490LV Scanning Electron Microscope were analyzed by image analysis for the size and coverage of pores. FIG. 6A and FIG. 6B are scanning electron microscopy (SEM) photomicrographs, showing 'raw' and 'detected' pores, respectively, for an exemplary surface of an elastomeric glove according to the present invention. FIG. 7A and FIG. 7B are representative images showing 'raw' and 'detected' pitting, respectively, for an exemplary commercially available nitrile-butadiene rubber medical exam glove (a Kimberly-Clark® Safeskin® PURPLE Nitrile® medical exam glove).

As can be observed from a comparison of the photomicrograph images, the Nitrile A glove surface appears to have a larger number of pores which covered more of the surface. The percentage of the measured surface area covered by pores, the equivalent circular diameter (ECD) of the pores as expressed in micrometers and the pore count data is are shown in Table 5.

TABLE 5

| Coverage and Sizing Data of Nitrile-butadiene rubber glove Surfaces | | | | | |
|---|---|---|---|---|---|
| Sample ID | % Pore Area | ECD (μm) | S. Dev. | Count/ FOV | Count/ mm$^2$ |
| Nitrile A | 3.94 | 5.84 | 3.30 | 685 | 1153 |
| Nitrile C | 1.53 | 5.04 | 2.45 | 400 | 673 |

The data confirmed the visual observations in showing that the Nitrile glove surface had larger pores and a greater number of pores relative to the Nitrile C glove surface. The percentage of pore surface area coverage of the Nitrile A glove sample surface was well over double the percentage of pore surface area coverage of the Nitrile C glove sample surface.

Figure 8A:
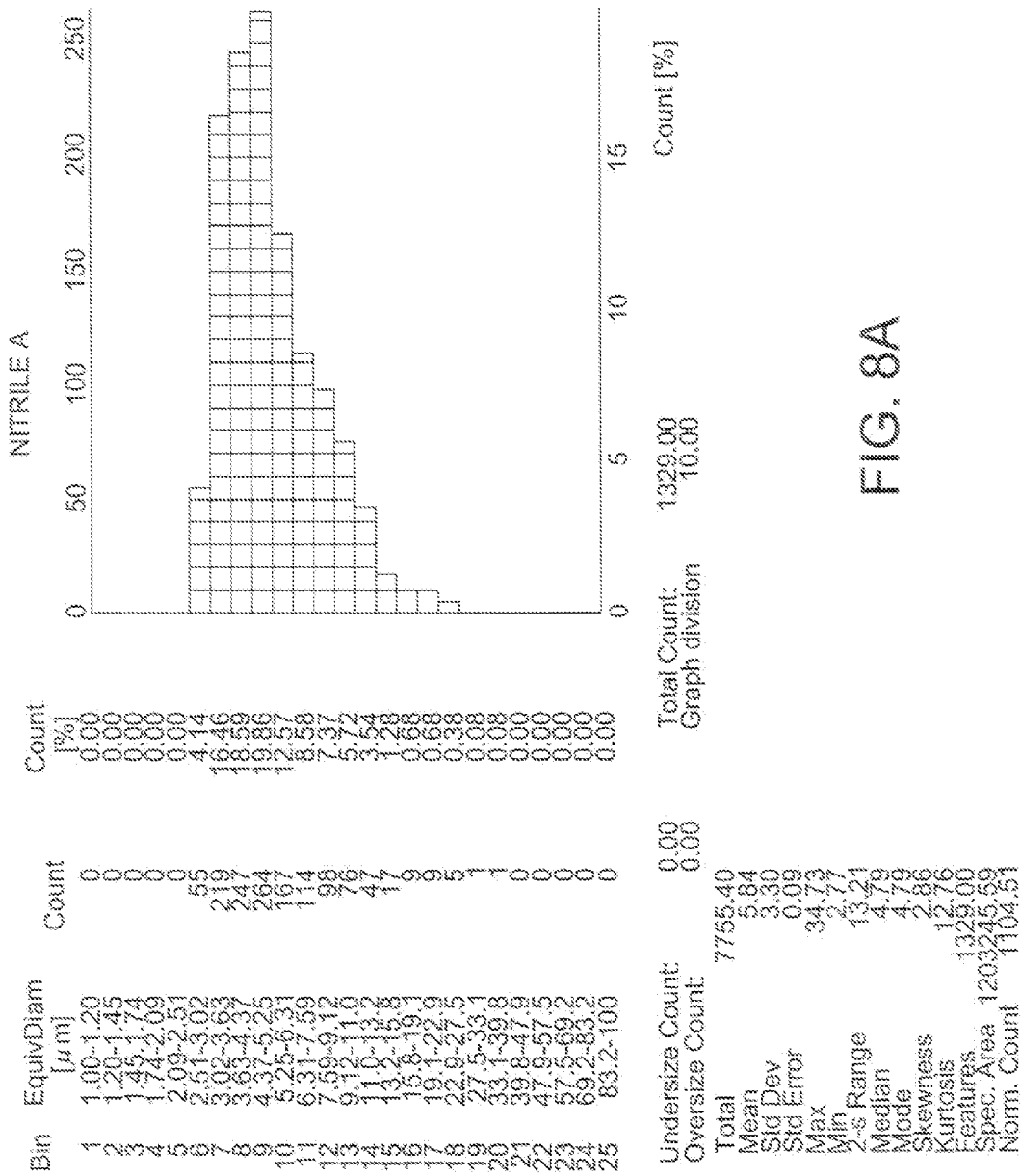
FIGS. 8A and 8B are histograms illustrating the frequency of pores having a specified equivalent circular diameter as determined by optical image analysis.
Figure 8B:
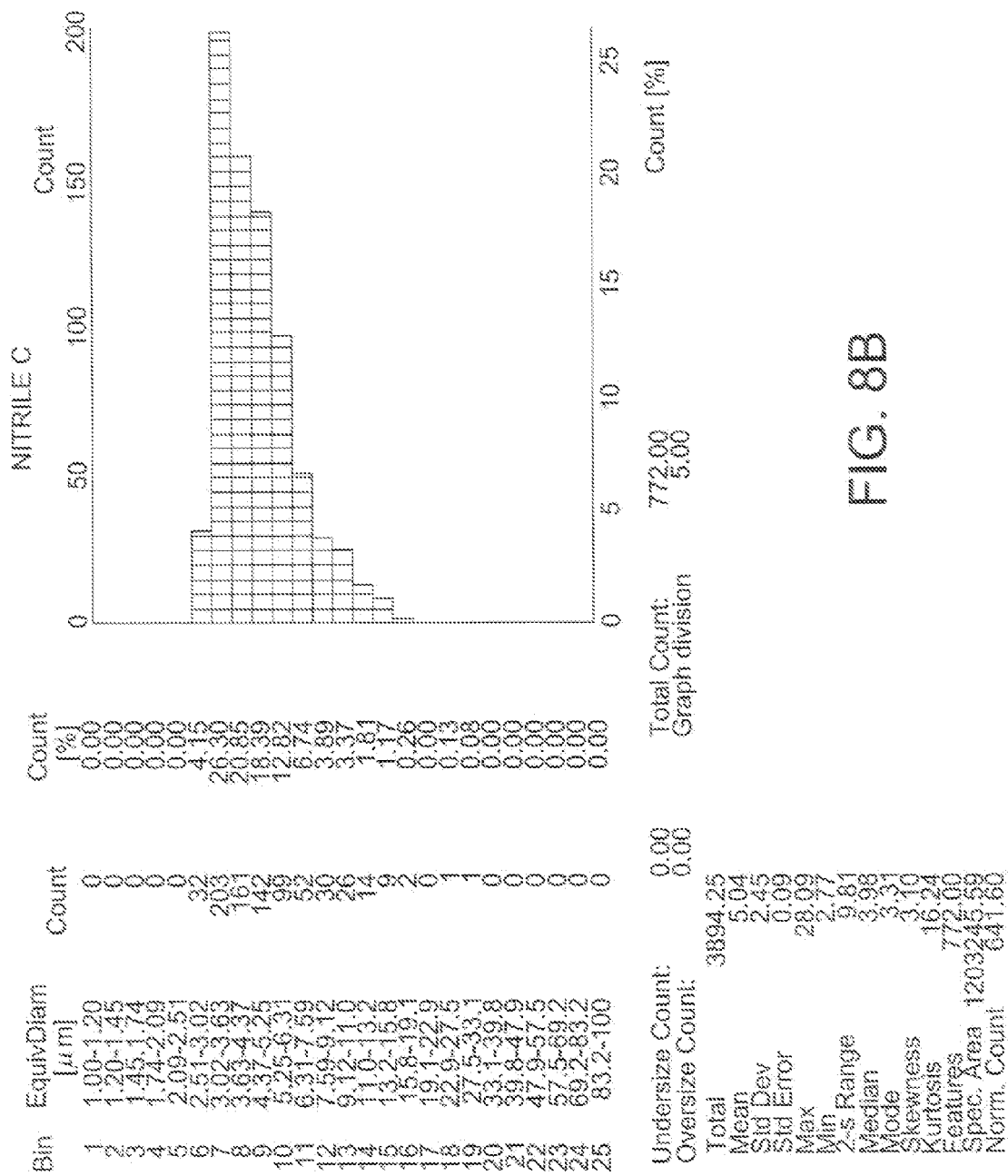

FIGS. 8A and 8B are histograms illustrating the frequency of pores having a specified equivalent circular diameter as determined by optical image analysis described above. FIG. 8A illustrates the frequency of pores having a specified equivalent circular diameter as determined by optical image analysis for an exemplary surface of an elastomeric glove according to the present invention (i.e., the Nitrile A glove). FIG. 8B illustrates the frequency of pores having a specified equivalent circular diameter as determined by optical image analysis for an exemplary commercially available nitrile-butadiene rubber medical exam glove (a Kimberly-Clark® Safeskin® PURPLE Nitrile® medical exam glove) which is referred to as the Nitrile C glove.

A Student's T analysis was performed on the ECD data at the 90% confidence level. The non-overlapping confidences ranges indicated that the mean values were different from each other and that Nitrile A glove exhibits a higher mean pore size value that the Nitrile C glove. For example, the Nitrile A glove exhibits a pore size range of from about 2.5 micrometers to about 27.5 micrometers and an average size 2-s range (2 standard deviations or 95%) of 13.2 micrometers. The Nitrile C glove exhibits a pore size range of from about 2.5 micrometers to about 19.1 micrometers and an average size 2-s range (2 standard deviations or 95%) of 9.8 micrometers.

FIG. 9 is a graph illustrating exemplary relationships between glove thickness and Water Vapor Transmission Rate for various sample nitrile-butadiene rubber gloves.

The Water Vapor Transmission Rate (WVTR) sometimes also called the Moisture Vapor Transmission Rate (MVTR) for the sample materials was measured and calculated in accordance with ASTM Standard E96-80. Circular samples having a specified diameter were cut from each of the test materials along with circular samples of the same diameter of a known control material. Three samples were prepared for each material. The control sample was run with each test and the preliminary test values were corrected to set conditions based on the performance of the control sample.

The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

We claim:

1. An elastomeric glove produced by a process comprising:
coating a surface of a mold with a coagulant solution and a release agent, the coagulation solution having a calcium ion concentration of between about 3 percent and about 5 percent based on the weight of calcium ions in the coagulant solution;
partially drying the mold coated with the coagulant solution and release agent;
immersing the partially dried mold into an nitrile-butadiene rubber latex emulsion having a latex solids content of between about 12 percent and about 20 percent, by weight, for a dwell time of between about 7 seconds and 15 seconds to form a layer of coagulated nitrile-butadiene rubber latex on the mold surface;
removing the mold from the nitrile-butadiene rubber latex emulsion;
immersing the mold containing the coagulated nitrile-butadiene rubber latex into an aqueous bath to remove excess calcium ions and then drying the coagulated nitrile-butadiene rubber latex to form a glove body on the mold;
immersing the mold containing the glove body into a chlorinating bath to chlorinate an exterior surface of the glove body on the mold; and
removing the glove body from the mold by inverting the glove body such that the chlorinated exterior surface of the glove body forms an interior surface of the glove body;
the elastomeric glove comprising a glove body consisting of a single, flexible layer of an elastomeric nitrile-butadiene rubber formed from a nitrile-butadiene rubber latex, the glove body having first surface forming a donning side of the glove body and an un-chlorinated second surface forming a grip side of the glove body;
a substantially uniform distribution of a waxy release agent over the un-chlorinated second surface of the glove body;
wherein the glove body has: (a) an average thickness of between about 0.03 to 0.12 mm in a palm region of the glove body; (b) an un-chlorinated second surface of the glove body characterized by a Surface Root Mean Square Roughness (Sq) of from about 3.00 µm to about 6.55 µm; and (c) a failure rate of less than about 1 percent when the elastomeric glove is subjected pinhole leak testing generally in accordance with ASTM D5151 06.

2. The elastomeric glove according to claim 1, wherein the glove body exhibits a force-to-strain response between zero elongation and 300 percent elongation (F-300) of less than or equal to about 1.50 N at F-300 when tested in accordance with ASTM D412-06.

3. The elastomeric glove according to claim 1, wherein the glove body exhibits a force-to-strain response between zero elongation and 300 percent elongation (F-300) that ranges from about 1.08 N to about 1.45 N for a thickness of about 0.03-0.10 mm when tested in accordance with ASTM D412-06.

4. The elastomeric glove according to claim 1, wherein the glove body exhibits a force-to-strain response between zero elongation and 400 percent elongation (F-400) of less than about 2 N at F-400 when tested in accordance with ASTM D412-06, or the glove body exhibits a force-to-strain response between zero elongation and 500 percent elongation (F-500) of less than about 2 N at F-500 when tested in accordance with ASTM D412-06.

5. The elastomeric glove according to claim 1, wherein the glove body exhibits a force to break of less than about 6.0 N at about 560 percent elongation to about 600 percent elongation of an original dimension when tested in accordance with ASTM D412-06.

6. The elastomeric glove according to claim 1, wherein the glove body has a surface area to volume ratio of between about 150/cm to about 250/cm.

7. The elastomeric glove according to claim 1, wherein the un-chlorinated second surface of the glove body is characterized by a Surface Root Mean Square Roughness (Sq) of from about 3.00 µm to about 5.30 µm.

8. The elastomeric glove according to claim 1, wherein the un-chlorinated second surface of the glove body is characterized by a Surface Average Roughness (Sa) of less than about 3.0 µm.

9. The elastomeric glove according to claim 1, wherein the un-chlorinated second surface of the glove body is characterized by a pore density ranging from about 820 pores per mm$^2$ to about 1600 pores per mm$^2$ as determined by optical image analysis.

10. The elastomeric glove according to claim 1, wherein the un-chlorinated second surface of the glove body is characterized by a pore density of greater than or equal to about 800 pores per mm$^2$ as determined by optical image analysis.

11. The elastomeric glove according to claim 1, wherein the release agent is selected from metallic stearates, petroleum waxes with a melting point of less than about 200° C., natural animal waxes, or synthetic waxes.

12. The elastomeric glove according to claim 1, wherein the elastomeric glove has a failure rate of less than about 0.5 percent when the elastomeric glove is subjected pinhole leak testing generally in accordance with ASTM D5151-06.

13. The elastomeric glove according to claim 1, wherein the elastomeric glove has a failure rate of less than about 0.1 percent when the elastomeric glove is subjected pinhole leak testing generally in accordance with ASTM D5151-06.

14. The elastomeric glove according to claim 1, wherein the elastomeric nitrile-butadiene rubber comprises a terpolymer of acrylonitrile, butadiene, and carboxylic acid in which the acrylonitrile polymer content is about 15 percent, by weight, to about 42 percent, by weight, the carboxylic acid content is between about 1 percent, by weight and about 10 percent by weight, and the remaining portion of the terpolymer composition is butadiene.

\* \* \* \* \*